(12) United States Patent
Gotoh et al.

(10) Patent No.: US 6,469,003 B1
(45) Date of Patent: Oct. 22, 2002

(54) PYRIDAZINONE DERIVATIVES

(75) Inventors: Makoto Gotoh, Osaka (JP); Koji Umimoto, Osaka (JP); Masanobu Onishi, Osaka (JP); Akiyuki Satoh, Mie (JP); Yoshitami Oshita, Osaka (JP); Masashi Nagamine, Nagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/762,877

(22) PCT Filed: Aug. 12, 1999

(86) PCT No.: PCT/JP99/04384

§ 371 (c)(1),
(2), (4) Date: Feb. 14, 2001

(87) PCT Pub. No.: WO00/09488

PCT Pub. Date: Feb. 24, 2000

(30) Foreign Application Priority Data

Aug. 14, 1998 (JP) ............................................ 10-229623

(51) Int. Cl.$^7$ ...................... A61K 31/50; C07D 237/14; C07D 401/12; C07D 401/14; C07D 403/17
(52) U.S. Cl. .................. 514/247; 514/248; 514/252.02; 514/252.03; 514/252.04; 514/252.05; 544/235; 544/238; 544/240
(58) Field of Search .................................. 544/238, 235, 544/240; 514/248, 247, 252.03, 252.02, 252.04, 252.05

(56) References Cited

FOREIGN PATENT DOCUMENTS

| EP | 0 711 759 A1 | 5/1996 |
|---|---|---|
| EP | 0 882 706 A1 | 12/1998 |
| JP | 62-223176 | 10/1987 |
| WO | 95/07264 | 3/1995 |

OTHER PUBLICATIONS

Shappell, et al; "Mac–1 (CD11b/CD118)Mediates Adherence–Dependent Hydrogen Peroxide Production by Human and Canine Neutrophils;" The Journal of Immunology; vol. 144, pp. 2702–2711, No. 7, Apr. 1, 1990.

Primary Examiner—Richard L. Raymond
(74) Attorney, Agent, or Firm—Sughrue Mion, PLLC

(57) ABSTRACT

A pyridazinone derivative represented by formula (I):

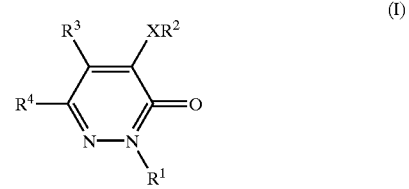

a pharmaceutically acceptable salt thereof, or a derivative thereof, or a pharmaceutical composition comprising as an active ingredient the derivative or a pharmaceutically acceptable salt thereof, and a pharmaceutically acceptable carrier or diluent.

5 Claims, No Drawings

PYRIDAZINONE DERIVATIVES

TECHNICAL FIELD

The present invention relates to a pyridazinone derivative having a cell adhesion inhibiting activity and useful for the treatment or prevention of inflammation, asthma, chronic articular rheumatism, arteriosclerosis, allergy, cancer metastasis, inflammatory disorder accompanying operation or treatment, ischemic reperfusion injury, rejection at organ transplantation, psoriasis, acute pulmonary injury, inflammatory intestinal disease, burn and the like, or pharmaceutically acceptable salt thereof, and a pharmaceutical composition comprising as an active ingredient the derivative or a pharmaceutically acceptable salt thereof.

BACKGROUND OF THE INVENTION

An inflammatory reaction is a sort of defense reaction which occurs at the time when a living body has received a stimulus caused by an alien substance, microbism or the like from the outside. At an inflammatory site, leukocytes which have infiltrated from blood vessels are observed, and the overresponse of the leukocytes causes tissue injury. The infiltration of leukocytes into tissues from blood vessels proceeds through several steps (*Cell*, 67, 1033–1036 (1991); *Immunol Today*, 14, 99–102 (1993); *Cell*, 76, 301–314 (1994)). For example, the infiltration of leukocytes into tissues at an inflammatory site observed mainly at early stage of inflammation is begun with the occurrence of adhesion of leukocytes circulating in blood vessels at physiological state to vascular endothelial cells. Since the phenomena of the adhesion of leukocytes to vascular endothelial cells and the infiltration into tissues are observed at chronic articular rheumatism, asthma, inflammatory intestinal disease, arteriosclerosis, and the like, the adhesion of leukocytes to vascular endothelial cells is considered to be an important step for the progress of these various diseases. (*Arthritis Rheum.*, 36, 147–157 (1993); *J. Clin. Invest.*, 93: 1411–1421 (1994); *The Journal of the Japanese Society of Internal Medicine*, 82: 1480–1485 (1993); *Nature*, 362: 801–809 (1993)).

Therefore, preventive or therapeutic effects on the above diseases including inflammation can be expected by inhibiting the adhesion of leukocytes to vascular endothelial cells. In fact, it has been reported that an antibody against an adhesion molecule of leukocytes such as LFA-1 or Mac-1, an antibody against ICAM-1 of a vascular endothelial cell or the like, suppresses the tissue infiltration of leukocytes in various laboratory animal models (*Science*, 255: 1125–1127 (1992); *Am. Rev. Respir. Dis.*, 147: 435–441 (1993)).

In addition, it has been revealed that derivatives of sialyl Lewis X which is sugar chain ligands of E-selectin are effective for inflammatory diseases as selectin inhibitors (Japan Society of Chest Disease (37th), 210 (1997)). However, these are used only limitedly owing to their antigenicity and low oral bioavailability. Therefore, some low molecular weight compounds have been reported for the purpose of overcoming these defects. For example, *The Year's Drug News* (p. 506, Prous Science (1995)) describes various low molecular weight compounds which exhibit a cell adhesion inhibiting activity. Furthermore, since cell adhesion of cancer cells acts an important role in their metastasis, inhibition of cell adhesion has been also thought to be effective in the cancer therapy (*Cancer Res.*, 82: 1120–1129 (1991); *Cancer Res.*, 53: 354–361 (1993)). In conclusion, the agents inhibiting cell adhesion are useful for the diseases mentioned above which are intractable and/or sufficient therapeutic methods are not established, because they have a different mode of action from that of pharmaceuticals hitherto employed.

DISCLOSURE OF THE INVENTION

An object of the present invention is to provide a pyridazinone derivative having a strong cell adhesion inhibiting activity and possessing an antiinflammatory activity, an antiasthmatic activity, an antirheumatic activity, an antiarteriosclerotic activity, an antiallergic activity, a suppressive activity of cancer metastasis, a suppressive activity of inflammatory disorder accompanying operation or treatment, a suppressive activity of ischemic reperfusion injury, a suppressive activity of rejection at organ transplantation, an antipsoriatic activity, a suppressive activity of acute pulmonary injury, a therapeutic activity of inflammatory intestinal disease, a therapeutic activity of burn and the like, or pharmaceutically acceptable salt thereof, and a medicament comprising as an active ingredient the derivative or a pharmaceutically acceptable salt thereof.

The present invention relates to a pyridazinone derivative represented by formula (I):

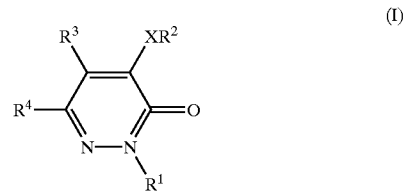

{wherein
R$^1$ represents a phenyl group, a substituted phenyl group, an aromatic heterocyclic group or a substituted aromatic heterocyclic group;
R$^2$ represents a (C$_1$–C$_8$)alkyl group, a substituted (C$_1$–C$_8$) alkyl group, a phenyl group, a substituted phenyl group, an aralkyl group, a substituted aralkyl group, an aromatic heterocyclic group, a substituted aromatic heterocyclic group, an amino group, an amino group substituted with one or two (C$_1$–C$_8$)alkyl groups which are the same or different, a 4- to 10-membered cyclic amino group, a cyano group, a carboxyl group, a (C$_1$–C$_8$)alkoxycarbonyl group, a carbamoyl group, a thiocarbamoyl group, an aminocarbonyl group, an aminocarbonyl group substituted with one or two (C$_1$–C$_8$) alkyl groups or substituted (C$_1$–C$_8$)alkyl groups which are the same or different, a 4- to 10-membered cyclic aminocarbonyl group, a phenylaminocarbonyl group, a substituted phenylaminocarbonyl group, an aromatic heterocyle-aminocarbonyl group or a substituted aromatic heterocyle-aminocarbonyl group;
R$^3$ represents a hydrogen atom, a (C$_1$–C$_8$)alkyl group, a substituted (C$_1$–C$_8$)alkyl group, a phenyl group, a substituted phenyl group, an aromatic heterocyclic group or a substituted aromatic heterocyclic group;
R$^4$ represents a cyano group,

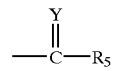

}

(wherein
R$^5$ represents a hydrogen atom, a (C$_1$–C$_8$)alkyl group, a substituted (C$_1$–C$_8$)alkyl group, a (C$_1$–C$_8$)alkoxy group, a hydroxyl group, amino group, an amino group substituted with one or two (C$_1$–C$_8$)alkyl groups which are the same or different, a 4- to 10-membered cyclic amino group, phenyl group, a substituted phenyl group, an aromatic heterocyclic group or a substituted aromatic heterocyclic group, or R$^5$ may form (CR$^7{}_2$)$_m$ (wherein R$^7$ are the same or different and represents hydrogen atom, a (C$_1$–C$_8$) alkyl group, a substituted (C$_1$–C$_8$)alkyl group, a phenyl group, a substituted phenyl group, an aromatic heterocyclic group or a substituted aromatic heterocyclic group, and m represent an integer of 2 to 7) together with R$^3$ to form a ring; and
Y represents NH, O or S),

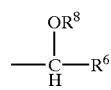

(wherein
R$^6$ represents a hydrogen atom, a (C$_1$–C$_8$)alkyl group, a substituted (C$_1$–C$_8$)alkyl group, a phenyl group, a substituted phenyl group, an aromatic heterocyclic group or a substituted aromatic heterocyclic group, or R$^6$ may form (CR$^7{}_2$)$_m$ (wherein R$^7$ and m have the same meanings as described above) together with R$^3$ to form a ring; and
R$^8$ represents a hydrogen atom or a (C$_1$–C$_8$) alkylcarbonyl group), or

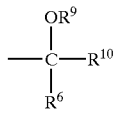

(wherein
R$^6$ has the same meaning as described above; and
R$^9$ and R$^{10}$ are the same or different and represent a (C$_1$–C$_8$)alkyl group or a substituted (C$_1$–C$_8$) alkyl group, or R$^9$ and R$^{10}$ together form a (C$_2$–C$_4$)alkylene chain and may form a ring together with the atoms attached thereto); and
X represents a single bond, O or S(O)$_n$ (wherein n represents an integer of 0, 1 or 2)},
or a pharmaceutically acceptable salt thereof.

Further, the present invention relates to a pharmaceutical composition comprising as an active ingredient the derivative or a pharmaceutically acceptable salt thereof, and a pharmaceutically acceptable carrier or diluent.

Furthermore, the present invention relates to use of the derivative or a pharmaceutically acceptable salt thereof as a cell adhesion inhibitor.

Moreover, the present invention relates to use of the derivative or a pharmaceutically acceptable salt thereof for manufacturing a medicament for the treatment or prevention of a disease relating to cell adhesion.

Also, the present invention relates to a method for inhibiting cell adhesion by administering an effective amount of the derivative or a pharmaceutically acceptable salt thereof.

Additionally, the present invention relates to a method for treating or preventing a disease relating to cell adhesion by administering an effective amount of the derivative or a pharmaceutically acceptable salt thereof.

BEST MODE FOR CARRYING OUT THE INVENTION

In order to solve the above problems, as a result of studies for the purpose of creating a pharmaceutical agent inhibiting cell adhesion, the present inventors have found that a pyridazinone derivative represented by formula (I) or a pharmaceutically acceptable salt thereof has an activity of strongly inhibiting the adhesion of leukocytes, and therefore accomplished the present invention.

The pyridazinone derivative represented by formula (I) can include optically active isomers depending on its substituents, and these isomers are also included in the present invention. In addition, the hydrates thereof are also included.

The terms in the present invention will be explained below.

In the present invention, the "cell adhesion inhibitor" means a pharmaceutical agent exhibiting a useful pharmacological activity directly or indirectly through inhibiting the process of cell adhesion. The cell adhesion inhibitor may be used preventively or therapeutically, and the examples of its use include an antiinflammatory agent, an antiasthmatic agent, an antirheumatic agent, an antiarteriosclerotic agent, an antiallergic agent, a suppressant of cancer metastasis, a suppressant of inflammatory disorder accompanying operation or treatment, a suppressant of ischemic reperfusion injury, a suppressant of rejection at organ transplantation, antipsoriatic agent, a suppressant of acute pulmonary injury, a remedy of inflammatory intestinal disease, a remedy of burn and the like, but the present invention is not limited thereto. The "disease relating to cell adhesion" includes mentioned inflammation, asthma, rheumatism, arteriosclerosis, allergy, cancer, inflammatory disorder accompanying operation or treatment, ischemic reperfusion injury, rejection at organ transplantation, psoriasis, acute pulmonary injury, inflammatory intestinal disease, burn and the like, but the present invention is not limited thereto.

In the definition of each group in formula (I), "(C$_1$–C$_8$)" means that the number of carbon atoms is from 1 to 8.

Among the substituents of R$^1$, R$^2$, R$^3$, R$^5$, R$^6$, R$^7$ and the like, the "substituted phenyl group" means a phenyl group having 1 to 5 substituents, which substitute the hydrogen atom(s) on the ring and are the same or different, selected from a (C$_1$–C$_8$)alkyl group, a halo(C$_1$–C$_8$)alkyl group, a (C$_1$–C$_8$)alkoxy group, a halo(C$_1$–C$_8$)alkoxy group, a (C$_1$–C$_8$)alkylthio group, a (C$_1$–C$_8$)alkoxycarbonyl group, a carbamoyl group, a cyano group, a nitro group, a halogen atom, a carboxyl group, a hydroxyl group, an amino group, an amino group, substituted with one or two (C$_1$–C$_8$)alkyl groups which are the same or different, a 4- to 10-membered cyclic amino group, an aminocarbonyl group substituted with one or two (C$_1$–C$_8$)alkyl groups which are the same or different, a 4- to 10-membered cyclic aminocarbonyl group, a (C$_1$–C$_8$)alkylcarbonylamino group, a (C$_1$–C$_8$) alkoxycarbonylamino group, a hydroxyamino group, an N-acetylhydroxyamino group, an acetoxyamino group, a methylenedioxy group, an ethylenedioxy group, a (C$_1$–C$_8$) alkylsulfonylamino group, a phenylcarbonylamino group, a phenylcarbonylamino group having 1 to 5 substituents, which are the same or different, selected from a (C$_1$–C$_8$) alkyl group, a (C$_1$–C$_8$)alkoxy group, a cyano group, a nitro group or a halogen atom on the ring, an aromatic heterocyclic-carbonylamino group, an aromatic heterocyclic-carbonylamino group having 1 to 5 substituents, which are the same or different, selected from a (C$_1$–C$_8$)alkyl group, a (C$_1$–C$_8$)alkoxy group, a cyano group, a nitro group or a halogen atom on the ring, a phenylsulfonylamino group, a phenylsulfonylamino group having 1 to 5 substituents, which are the same or different, selected from a ($C_1$–$C_8$)alkyl group, a ($C_1$–$C_8$)alkoxy group, a cyano group, a nitro group or a halogen atom on the ring, an aromatic heterocyclic-sulfonylamino group, an aromatic heterocyclic-sulfonylamino group having 1 to 5 substituents, which are the same or different, selected from a ($C_1$–$C_8$) alkyl group, a ($C_1$–$C_8$)alkoxy group, cyano group, nitro group or a halogen atom on the ring. Specific examples include a 2-methylphenyl group, a 3-methylphenyl group, a 4-methylphenyl group, a 4-tert-butylphenyl group, a 2-methoxyphenyl group, a 3-methoxyphenyl group, a 4-methoxyphenyl group, a 3,4-dimethoxyphenyl group, a 4-trifluoromethylphenyl group, a 4-trifluoromethoxyphenyl group, a 2-methylthiophenyl group, a 4-methylthiophenyl group, a 4-trifluoromethylthiophenyl group, a 2-methoxycarbonylphenyl group, a 3-methoxycarbonylphenyl group, a 4-methoxycarbonylphenyl group, a 2-carbamoylphenyl group, a 3-carbamoylphenyl group, a 4-carbamoylphenyl group, a 2-cyanophenyl group, a 3-cyanophenyl group, a 4-cyanophenyl group, a 2-nitrophenyl group, a 3-nitrophenyl group, a 4-nitrophenyl group, a 2-fluorophenyl group, a 3-fluorophenyl group, a 4-fluorophenyl group, a 2,4-difluorophenyl group, a 2-chlorophenyl group, a 3-chlorophenyl group, a 4-chlorophenyl group, a 2,4-dichlorophenyl group, a 3,4-dichlorophenyl group, a 2-bromorophenyl group, a 3-bromorophenyl group, a 4-bromorophenyl group, a 2-carboxyphenyl group, a 3-carboxyphenyl group, a 4-carboxyphenyl group, a 2-hydroxyphenyl group, a 3-hydroxyphenyl group, a 4-hydroxyphenyl group, a 3,5-di-tert-butyl-4-hydroxyphenyl group, a 2-aminophenyl group, a 3-aminophenyl group, a 4-aminophenyl group, a 4-methylaminophenyl group, a 4-dimethylaminophenyl group, a 4-pyrrolidinophenyl group, a 4-methylaminocarbonylphenyl group, a 4-dimethylaminocarbonylphenyl group, a 4-acetylaminophenyl group, a 4-ethoxycarbonylamino group, a 4-pyrrolidinocarbonylphenyl group, a 4-hydroxyaminophenyl group, a 4-acetylhydroxyaminophenyl group, a 4-acetoxyaminophenyl group, a 3,4-methylenedioxyphenyl group, a 3,4-ethylenedioxyphenyl group, a 4-methylsulfonylaminophenyl group, a 4-phenylsulfonylaminophenyl group, a 4-phenylcarbonylaminophenyl group, a 4-methylphenylcarbonylaminophenyl group, a 4-methoxyphenylcarbonylaminophenyl group, a 4-cyanophenylcarbonylaminophenyl group, a 4-nitrophenylcarbonylaminophenyl group, a 4-fluorophenylcarbonylaminophenyl group, a 2-furylcarbonylaminophenyl group, a 2-thienylcarbonylaminophenyl group, and the like.

Examples of the "aromatic heterocyclic group" include a 2-furyl group, a 3-furyl group, a 2-thienyl group, a 3-thienyl group, a 2-pyrrolyl group, a 2-pyridyl group, a 3-pyridyl group, a 4-pyridyl group, a 2-pyridyl N-oxide group, a 3-pyridyl N-oxide group, a 4-pyridyl N-oxide group, a 2-oxazolyl group, a 3-isoxazolyl group, a 2-thiazolyl group, a 4-thiazolyl group, a 5-thiazolyl group, a 2-imidazolyl group, a 3-pyrazolyl group, a 2-pyrimidinyl group, a 3-pyridazinyl group, a 2-pyrazinyl group, a 2-(1,3,5-triazinyl) group, a 3-(1H-1,2,4-triazolyl) group, a 5-(1H-tetrazolyl) group, a 2-indolyl group, a 8-quinolyl group, a 2-purinyl group and the like. These can include benzo derivatives, and examples include, a 2-benzoxazolyl group, a 2-benzothiazolyl group, a 2-benzimidazolyl group and the like.

The "substituted aromatic heterocyclic group" means a substituted aromatic heterocyclic group having 1 to 5 substituents, which are the same or different, selected from a ($C_1$–$C_8$)alkyl group, a ($C_1$–$C_8$)alkoxy group, a ($C_1$–$C_8$) alkylthio group, a ($C_1$–$C_8$)alkoxycarbonyl group, a carboxyl group, a carbamoyl group, a cyano group, a nitro group or a halogen atom, and examples include a 4-methyl-5-thiazolyl group, a 6-methyl-2-pyridyl group, a 3-methoxy-4-pyridyl group, a 6-methoxy-3-pyridyl group, a 6-methylthio-3-pyridyl group, a 4-ethoxycarbonyl-2-thienyl group, a 4-carboxy-2-thienyl group, a 4-chloro-2-pyridyl group, a 4-chloro-3-pyridyl group, 2-chloro-3-pyridyl group, a 6-chloro-3-pyridyl group, a 2-cyano-4-pyridyl group, a 2-cyano-3-pyridyl group, a 6-cyano-3-pyridyl group, a 3-carboxy-2-pyridyl group, a 5-carboxy-2-pyridyl group, a 2-carboxy-4-pyridyl group, a 2-carboxy-3-pyridyl group, a 6-carboxy-3-pyridyl group, a 6-methyl-2-pyridyl N-oxide group, a 4-chloro-2-pyridyl N-oxide group, a 6-methoxy-3-pyridyl N-oxide group, a 4-ethoxycarbonyl-2-thiazolyl group, a 4-carboxy-2-thiazolyl group, a 1-methyl-2-imidazolyl group, a 5-methyl-2-(1,3,4-thiadiazolyl) group, a 4-methyl-3-(4H-1,2,4-triazolyl) group, a 1-methyl-5-(1H-tetrazolyl) group and the like.

The "($C_1$–$C_8$)alkyl group" means a "linear, branched or cyclic" alkyl group, and examples include a methyl group, an ethyl group, a propyl group, an isopropyl group, a cyclopropyl group, a butyl group, an isobutyl group, a sec-butyl group, a tert-butyl group, a cyclobutyl group, a pentyl group, an isopentyl group, a neopentyl group, a cyclopentyl group, a hexyl group, a cyclohexyl group, a cycloheptyl group, an octyl group, a cyclooctyl group and the like.

The "substituted ($C_1$–$C_8$)alkyl group" means an alkyl group substituted with one or more substituents, which are the same or different, selected from a halogen atom, a hydroxyl group, a ($C_1$–$C_8$)alkoxy group, a ($C_1$–$C_8$)alkylthio group, a ($C_1$–$C_8$)alkoxycarbonyl group, a carboxyl group, a cyano group, a nitro group, an amino group, a hydroxyamino group, an amino group substituted with one or two ($C_1$–$C_8$) alkyl groups which are the same or different, a 4- to 10-membered cyclic amino group, a ($C_1$–$C_8$) alkxvlcarbonylamino group, a carbamoyl group, an aminocarbonyl group substituted with one or two ($C_1$–$C_8$)alkyl groups which are the same or different a 4- to 10-membered cyclic aminocarbonyl group, a ($C_1$–$C_8$)alkylsulfonylamino group, a phenylcarbonylamino group, a phenylcarbonylamino group having 1 to 5 substituents, which are the same or different, selected from a ($C_1$–$C_8$)alkyl group, a ($C_1$–$C_8$) alkoxy group, a ($C_1$–$C_8$)alkoxycarbonyl group, a cyano group, a nitro group or a halogen atom on the ring, an aromatic heterocyclic-carbonylamino group, an aromatic heterocyclic-carbonylamino group having 1 to 5 substituents, which are the same or different, selected from a ($C_1$–$C_8$)alkyl group, a ($C_1$–$C_8$)alkoxy group, a ($C_1$–$C_8$) alkoxycarbonyl group, a cyano group, a nitro group or a halogen atom on the ring, a phenylsulfonylamino group, a phenylsulfonylamino group having 1 to 5 substituents, which are the same or different, selected from a ($C_1$–$C_8$) alkyl group, a ($C_1$–$C_8$)alkoxy group, a ($C_1$–$C_8$) alkoxycarbonyl group, a cyano group, a nitro group or a halogen atom on the ring, an aromatic heterocyclic-sulfonylamino group, an aromatic heterocyclic-sulfonylamino group having 1 to 5 substituents, which are the same or different, selected from a ($C_1$–$C_8$)alkyl group, a ($C_1$–$C_8$)alkoxy group, a ($C_1$–$C_8$)alkoxycarbonyl group, a cyano group, a nitro group or a halogen atom on the ring, and examples include a fluoromethyl group, a difluoromethyl group, a trifluoromethyl group, a hydroxymethyl group, a hydroxyethyl group, a hydroxypropyl group, a methoxymethyl group, a methoxyethyl group, a carboxymethyl group, a carboxyethyl group, a methoxycarbonylmethyl group, an ethoxycarbonylmethyl group, a methoxycarbonylethyl group, a an ethoxycarbonylethyl group, an aminomethyl group, an aminoethyl group, an aminopropyl group, a hydroxyaminoethyl group, a hydroxyaminopropyl group, a methylaminomethyl group, a methylaminoethyl group, a dimethylaminomethyl group, a dimethylaminoethyl group, a pyrrolidinoethyl group, a piperidinoethyl group, a 1-methyl-4-piperidino group, an acetylaminoethyl group, a formamidoethyl group, a carbamoylmethyl group, a carbamoylethyl group, a methylaminocarbonylmethyl group, a dimethylaminocarbonylethyl group, a piperidinocarbonylmethyl group, a methylsulfonylaminoethyl group, a phenylcarbonylaminoethyl group, a phenylsulfonylaminoethyl group and the like.

The "aralkyl group" means an alkyl group having 1 to 8 carbon atoms substituted with an aryl group having 7 to 15 carbon atoms or an aromatic heterocyclic group, and the "aryl" moiety includes phenyl, naphthyl, anthranyl and the like, the definition of the aromatic heterocyclic group being the same as described above. Examples of the "aralkyl group" include a benzyl group, a phenethyl group, a 2-phenylpropyl group, a 2-pyridylmethyl group, a 3-pyridylmethyl group, a 4-pyridylmethyl group, a 2-pyridylmethyl N-oxide group, a 3-pyridylmethyl N-oxide group, a 4-pyridylmethyl N-oxide group, a 2-thienylmethyl group, a 3-thienylmethyl group, a 2-thienylethyl group, a 3-thienylethyl group, a 2-furylmethyl group, a 3-furylmethyl group, a 2-furylethyl group, a 3-furylethyl group, a 2-quinoxalylmethyl group, a 3-indolylethyl group and the like.

The "substituted aralkyl group" can be an aralkyl group having an aryl ring or aromatic heterocycle substituted with 1 to 5 substituents, which are the same or different, selected from a ($C_1$–$C_8$)alkyl group, a ($C_1$–$C_8$)alkoxy group, a ($C_1$–$C_8$)alkoxycarbonyl group, a carboxyl group, a cyano group, a nitro group or a halogen atom, and examples include a 4-methylbenzyl group, a 4-methoxybenzyl group, a 4-fluorobenzyl group, a (4-methyl-5-thiazolyl)ethyl group, a (4-chloro-2-pyridyl)methyl group, a (4-chloro-2-pyridyl)methyl N-oxide group, a (6-methyl-2-pyridyl)methyl group, a (6-methyl-2-pyridyl)methyl N-oxide group, a (5-chloro-2-pyridyl)methyl group, a (5-chloro-2-pyridyl)methyl N-oxide group, a (2,6-dichloro-4-pyridyl)methyl group, a (2-cyano-4-pyridyl)methyl group, a (2-carboxy-4-pyridyl)methyl group, a (5-methoxy-3-indol)methyl group, a (5-bromo-3-indol)ethyl group, a (3,5-dimethyl-4-pyrazolyl)methyl group, a (3-methyl-2-thienyl)methyl group and the like.

The "amino group substituted with one or two $C_1$–$C_8$ alkyl groups which are the same or different" means an amino group substituted with one or two groups, which are the same or different, selected from the alkyl groups having the same meaning as the above-described "($C_1$–$C_8$)alkyl group", and examples include a methylamino group, a dimethylamino group, an ethylamino group, a diethylamino group, a methylethylamino group, a propylamino group, a dipropylamino group, an isopropylamino group, a diisopropylamino group, a butylamino group, a dibutylamino group and the like. Moreover, the amino group substituted with two groups selected from ($C_1$–$C_8$)alkyl groups can be further substituted with a ($C_1$–$C_8$)alkyl group, a substituted ($C_1$–$C_8$)alkyl group, an aralkyl group or a substituted aralkyl group to form an ammonium base, and examples include a trimethylammonium base, a triethylammonium base, a benzyldimethylammonium base and the like.

The "4- to 10-membered cyclic amino group" means a cyclic amino group which can contain a nitrogen atom, an oxygen atom or a sulfur atom, and examples include a pyrrolidino group, a piperidino group, a piperazino group, an N-methylpiperazino group, an N-phenylpiperazino group, a morpholino group, a thiomorpholino group, a hexamethyleneimino group, a 3,3,5-trimethylhexahydroazepino group and the like. Moreover, the cyclic amino group can form a quaternary base further substituted with a ($C_1$–$C_8$)alkyl group, a substituted ($C_1$–$C_8$) alkyl group, an aralkyl group or a substituted aralkyl group, and examples include a methylpyrrolidinium base, a methylpiperidinium base, a methylmorpholinium base and the like.

The "($C_1$–$C_8$)alkoxycarbonyl group" means a carbonyl group having a "linear, branched or cyclic" alkoxy group having 1 to 8 carbon atoms, and examples include a methoxycarbonyl group, an ethoxycarbonyl group, a propoxycarbonyl group, an isopropoxycarbonyl group, a tert-butoxycarbonyl group, a cyclopropylcarbonyl group and the like.

The "aminocarbonyl group substituted with one or two ($C_1$–$C_8$)alkyl groups or substituted ($C_1$–$C_8$)alkyl groups which are the same or different" means an aminocarbonyl group substituted with one or two groups, which are the same or different, selected from the alkyl groups having the same meaning as the above-described "($C_1$–$C_8$)alkyl group" or "substituted ($C_1$–$C_8$)alkyl group", and examples include a methylaminocarbonyl group, a dimethylaminocarbonyl group, an ethylaminocarbonyl group, an ethylmethylaminocarbonyl group, a propylaminocarbonyl group, an isopropylaminocarbonyl group, a cyclopropylaminocarbonyl group, a hydroxymethylaminocarbonyl group, a methoxymethylaminocarbonyl group, a carboxymethylaminocarbonyl group, a carbamoylmethylaminocarbonyl group and the like.

The "4- to 10-membered cyclic aminocarbonyl group" means a carbonyl group having the cyclic amino group having the same meaning as the above-described "4- to 10-membered cyclic amino group", and examples include a pyrrolidinocarbonyl group, a piperidinocarbonyl group, a piperazinocarbonyl group, an N-methyl-piperazinocarbonyl group, an N-phenyl-piperazinocarbonyl group, a morpholinocarbonyl group, a thiomorpholinocarbonyl group and the like.

The "substituted phenylaminocarbonyl group" means an aminocarbonyl group having the phenyl group having the same meaning as the above-described "substituted phenyl group", and the examples include a phenylaminocarbonyl group, a 4-methylphenylaminocarbonyl group, a 4-methoxyphenylaminocarbonyl group, a 4-methylthiophenylaminocarbonyl group, a 4-chlorophenylaminocarbonyl group, a 4-cyanophenylaminocarbonyl group and the like.

The "aromatic heterocyle-aminocarbonyl group" means an aminocarbonyl group having the aromatic heterocyclic group of the same meaning as the above-described "substituted aromatic heterocyclic group", and examples include a 2-pyridylaminocarbonyl group, a 3-pyridylaminocarbonyl group, a 4-pyridylaminocarbonyl group, a 2-thiazolylaminocarbonyl group and the like.

The "substituted aromatic heterocyle-aminocarbonyl group" means an aminocarbonyl group having the aromatic heterocyclic group of the same meaning as the above-described "substituted aromatic heterocyclic group", and examples include a 4-methyl-5-thiazolylaminocarbonyl group, a 6-methyl-2-pyridylaminocarbonyl group and the like.

The "$(C_1-C_8)$alkoxy group" means a "linear, branched or cyclic" alkoxy group having 1 to 8 carbon atoms, and examples include a methoxy group, an ethoxy group, a propoxy group, an isopropoxy group, a butoxy group, an isobutoxy group, a cyclopropylmethoxy group, a pentyloxy group, a hexyloxy group, a heptyloxy group, an octyloxy group and the like.

The "halogen atom" means each atom of fluorine, chlorine, bromine, and iodine.

The "$(C_1-C_8)$alkylcarbonyl group" means a carbonyl group having the alkyl group of the same meaning as the above-described "$(C_1-C_8)$alkyl group", and examples include an acetyl group, a propionyl group, a butyryl group, an isobutyryl group, a valeryl group, an isovaleryl group, a pentylcarbonyl group, a hexylcarbonyl group, a heptylcarbonyl group, an octylcarbonyl group and the like.

The "halo$(C_1-C_8)$alkyl group" means a "linear, branched or cyclic" alkyl group having 1 to 8 carbon atoms substituted with one or more halogen atoms which are the same or different, and examples include a chloromethyl group, a dichloromethyl group, a trichloromethyl group, a fluoromethyl group, a difluoromethyl group, a trifluoromethyl group, a 2,2,2-trifluoroethyl group and the like.

The "halo$(C_1-C_8)$alkoxy group" means a "linear, branched or cyclic" alkoxy group having 1 to 8 carbon atoms substituted with one or more halogen atoms which are the same or different, and examples include a chloromethoxy group, a dichloromethoxy group, a trichloromethoxy group, a fluoromethoxy group, a difluoromethoxy group, a trifluoromethoxy group and the like.

The "$(C_1-C_8)$alkylthio group" means a "linear, branched or cyclic" alkylthio group having 1 to 8 carbon atoms, and examples include a methylthio group, an ethylthio group, a propylthio group, an isopropylthio group, a butylthio group and the like.

The "$(C_1-C_8)$alkylcarbonylamino group" means an amino group having the alkylcarbonyl group of the same meaning as the above-described "$(C_1-C_8)$ alkylcarbonyl group", and examples include a methylcarbonylamino group, an ethylcarbonylamino group, a propylcarbonylamino group, an isopropylcarbonylamino group, a butylcarbonylamino group, a pentylcarbonylamino group, a hexylcarbonylamino group, a heptylcarbonylamino group, an octylcarbonylamino group and the like.

The "$(C_1-C_8)$alkoxycarbonylamino group" means an amino group having the alkoxycarbonyl group of the same meaning as the above-described "$(C_1-C_8)$alkoxycarbonyl group", and examples include a methoxycarbonylamino group, an ethoxycarbonylamino group, a propoxycarbonylamino group, an isopropoxycarbonylamino group, a tert-butoxycarbonylamino group and the like.

The "$(C_1-C_8)$alkylsulfonylamino group" means a sulfonylamino group having the alkyl group of the same meaning as the above-described "$(C_1-C_8)$alkyl group", and examples include a methylsulfonylamino group, an ethylsulfonylamino group, a propylsulfonylamino group, an isopropylsulfonylamino group, a butylsulfonylamino group, a pentylsulfonylamino group, a hexylsulfonylamino group and the like.

The "phenylcarbonylamino group, aromatic heterocyclic-carbonylamino group, phenylsulfonylamino group or aromatic heterocyclic-sulfonylamino group having 1 to 5 substituents selected from a $(C_1-C_8)$alkyl group, a $(C_1-C_8)$alkoxy group, a cyano group, a nitro group or a halogen atom on the ring" means a carbonylamino group and sulfonylamino group having a phenyl group or an aromatic heterocyclic group substituted with 1 to 5 groups, which are the same or different, selected from the alkyl group, alkoxy group and halogen atom having the same meaning as the above-described "$(C_1-C_8)$alkyl group", "$(C_1-C_8)$alkoxy group" and "halogen atom". Examples thereof include a phenylcarbonylamino group, a 4-methylphenylcarbonylamino group, a 4-methoxyphenylcarbonylamino group, a 4-fluorophenylcarbonylamino group, a 4-chlorophenylcarbonylamino group, a 2-methyl-3-pyridylcarbonylamino group, a 6-methyl-3-pyridylcarbonylamino group, a 2-chloro-3-pyridylcarbonylamino group, a 6-methyl-3-pyridylcarbonylamino group, a 4-methylphenylsulfonylamino group, a 4-methoxyphenylsulfonylamino group, a 4-fluorophenylsulfonylamino group, a 4-chlorophenylsulfonylamino group and the like.

Examples of the "pharmaceutically acceptable salt" of the pyridazinone derivative represented by formula (I) in the present invention include inorganic salts, such as hydrochlorides, sulfates, nitrates, phosphates and the like, organic salts, such as acetates, fumarates, maleates, tartarates, citrates, lactates, oxalates, methansulfonates, benzenesulfonates, p-toluenesulfonates, and salts with metal ions, such as sodium ion, potassium ion, calcium ion and the like.

The pyridazinone derivative represented by formula (I) can be produced according to the following Production Methods 1 to 13, for example. In the formulae of the following Production Methods, $R^1$, $R^2$, $R^3$, $R^4$, $R^5$, $R^6$, $R^9$, $R^{10}$ and X have the same meanings as described above. A represents a halogen atom; E represents a halogen atom or a $(C_1-C_8)$alkoxy group; $R^{11}$ represents a $(C_1-C_8)$alkyl group, a substituted $(C_1-C_8)$alkyl group, a phenyl group, a substituted phenyl group, an aralkyl group, a substituted aralkyl group, an aromatic heterocyclic group or a substituted aromatic heterocyclic group; G represents O or S; $NR^{12}R^{13}$ represents an amino group, an amino group substituted with one or two groups, which are the same or different, selected from $(C_1-C_8)$alkyl groups, or a 4- to 10-membered cyclic amino group; J represents a $(C_1-C_8)$ alkoxy group; L represents a hydroxyl group or a $(C_1-C_8)$ alkoxy group; M represents a hydrogen atom, a hydroxyl group, a $(C_1-C_8)$alkyl group, a substituted $(C_1-C_8)$alkyl group, a $(C_1-C_8)$alkoxy group or a substituted $(C_1-C_8)$ alkoxy group; Q represents a $(C_1-C_8)$alkylcarbonyl group. Each definition of the halogen atom, $(C_1-C_8)$alkoxy group, $(C_1-C_8)$alkyl group, substituted $(C_1-C_8)$alkyl group, phenyl group, substituted phenyl group, aralkyl group, substituted aralkyl group, aromatic heterocyclic group, substituted aromatic heterocyclic group, amino group substituted with one or two groups, which are the same or different, selected from $(C_1-C_8)$alkyl groups, or a 4- to 10-membered cyclic amino group has the same meaning as described above. T represents a pyridyl group or a substituted pyridyl group, U represents a pyridyl N-oxide group or a substituted pyridyl N-oxide group, the substituent(s) of the substituted pyridyl group or substituted pyridyl N-oxide group having the same meaning as the substituent(s) of the substituted aromatic heterocyle. V represents a methyl group or an ethyl group and p represents an integer of 1 or 2.

The methods for producing the compounds of the present invention are shown below; however, the present invention is not limited thereto.

Production Example 1

Step A

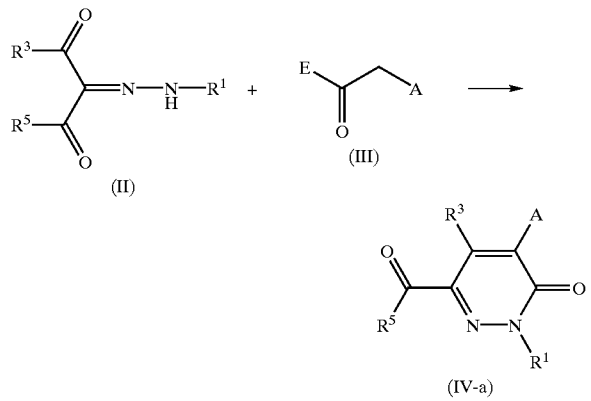

Step B

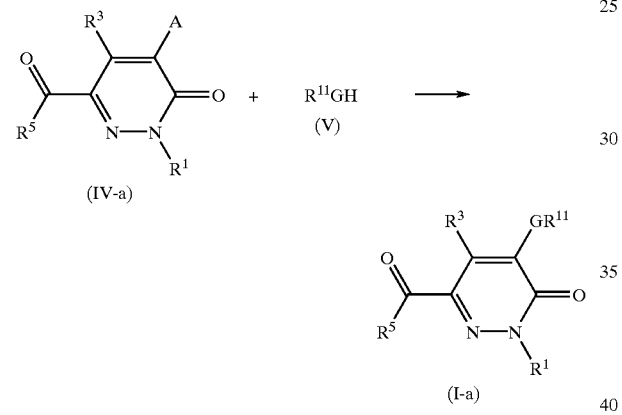

Step A

Compound (IV-a) can be produced according to known methods (*Synthesis*, 91 (1997); *Tetrahedron*, 51: 12745 (1995); *J. Indian Chem. Soc.*, 69: 314 (1992); *J. Serb. Chem. Soc.*, 57: 725 (1992); *Indian J. Chem. SectB.*, 31B: 273 (1992); *Synth. Commun.*, 21: 1935 (1991); *Synth. Commun.*, 21: 1021 (1992); *Liebig. Ann. Chem.*, 10: 1005 (1988); *Tetrahedron Lett.*, 21: 2939 (1980); *J. Heterocyclic Chem.*, 18: 333 (1981)) or from Compound (II) obtainable according to the methods described in these literatures and Compound (III) by use of a known method (*Indian J. Chem. SectB.*, 31B: 273 (1992)) or a method based on the method described in the literature. Compound (III) is commercially available (for example, a product of Aldrich Company or the like) or can be produced according to a known method (*Beil.*, 2: 199, 215) or based on the method described therein.

Step B

Compound (I-a) can be produced by reacting Compound (IV-a) obtained in Step A and Compound (V) usually at 0° C. to room temperature for 1 to 24 hours in the presence or absence of an inert solvent and in the presence of a base using a phase transfer catalyst, copper powder, a copper(I) halide and the like, if necessary. Examples of the inert solvent include alcohols such as methanol and ethanol, ethers such as tetrahydrofuran, diethyl ether and dioxane, hydrocarbons such as toluene and benzene, halogenated hydrocarbons such as dichloromethane, chloroform and 1,2-dichloroethane, ketone-type solvents such as acetone and methyl ethyl ketone, polar organic solvents such as acetonitrile, N,N-dimethylformamide and dimethyl sulfoxide, water or mixed solvents thereof. Examples of the base include nitrogen-containing organic bases such as triethylamine, diisopropylethylamine and pyridine, inorganic bases such as potassium carbonate, sodium hydrogen carbonate, sodium hydroxide, sodium hydride and metallic sodium, organic bases such as sodium acetate, potassium acetate and ammonium acetate, alcoholates such as potassium t-butoxide and sodium ethoxide. The phase transfer catalyst can be exemplified by quaternary ammonium salts such as benzyltriethylammonium bromide, and crown ethers such as 18-crown-6-ether.

Production Method 2

Step C

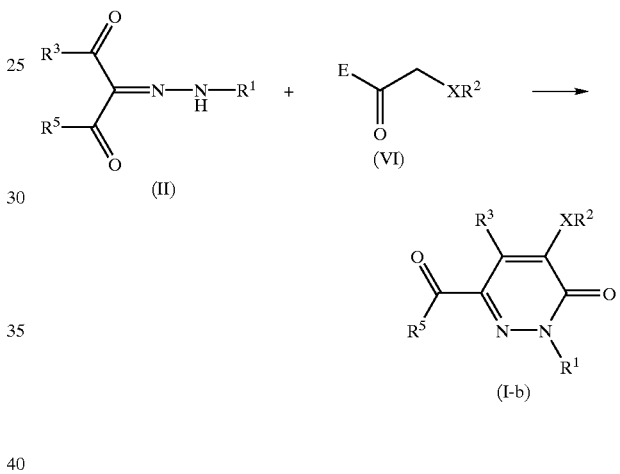

Step C

Compound (I-b) can be produced by reacting Compound (II) and Compound (VI) usually at 0° C. to 100° C. for 1 to 24 hours in the presence or absence of an inert solvent and in the presence of a base. Examples of the inert solvent include alcohols such as methanol and ethanol, ethers such as tetrahydrofuran, diethyl ether and dioxane, hydrocarbons such as toluene and benzene, halogenated hydrocarbons such as dichloromethane, chloroform and 1,2-dichloroethane, ketone-type solvents such as acetone, organic polar solvents such as acetonitrile, N,N-dimethylformamide and dimethyl sulfoxide, water or mixed solvents thereof.

Examples of the base include nitrogen-containing organic bases such as triethylamine, diisopropylethylamine, piperidine, morpholine and pyridine, inorganic bases such as potassium carbonate, sodium hydrogen carbonate, sodium hydroxide, sodium hydride and metallic sodium, alcoholates such as potassium t-butoxide and sodium ethoxide, organic bases such as sodium acetate, potassium acetate and ammonium acetate. Compound (VI) is commercially available (for example, a product of Aldrich Company or the like) or can be produced according to a known method (*Beil.*, 6: 162) or based on the method.

Production Method 3

Step D

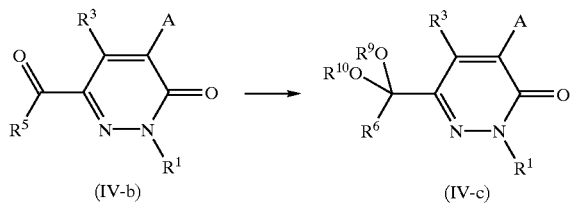

Step E

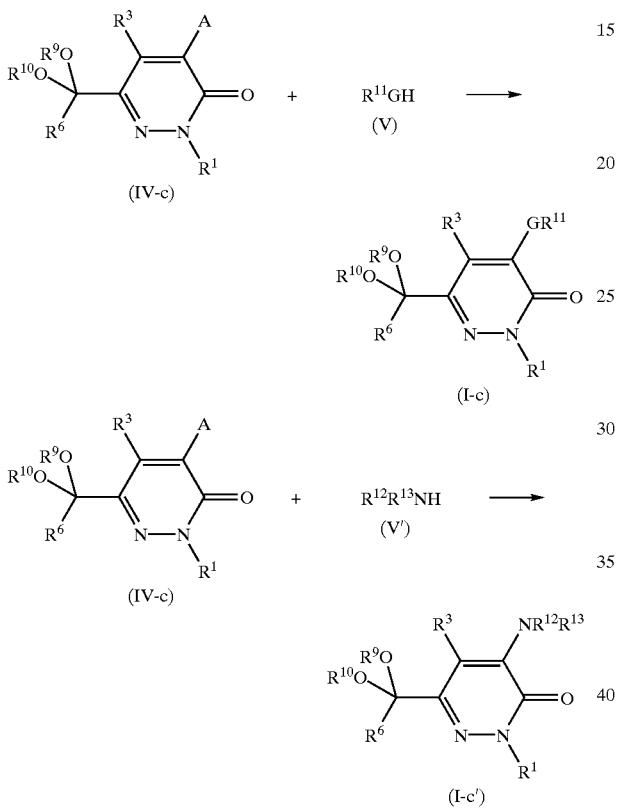

Step D

Compound (IV-c) can be produced by reacting Compound (IV-b) produced according to the method of Step A with an alcohol such as ethylene glycol usually at room temperature to the boiling point of the solvent for 1 to 48 hours under the usual conditions for protecting a carbonyl group, for example, in the presence of an organic acid catalyst such as p-toluenesulfonic acid in an aromatic hydrocarbon such as toluene or benzene with removing water formed during the reaction by means of a water-separating apparatus, distillation, a Lewis acid such as boron trifluoride, or a dehydrating agent such as an orthoester.

Step E

Compound (I-c or I-c') can be produced by reacting Compound (IV-c) produced in above Step D and Compound (V or V') usually at 0° C. to room temperature for 1 to 24 hours in the presence or absence of an inert solvent and in the presence of a base using a phase transfer catalyst, copper powder, a copper (I) halide and the like, if necessary. Examples of the inert solvent include alcohols such as methanol and ethanol, ethers such as tetrahydrofuran, diethyl ether and dioxane, hydrocarbons such as toluene and benzene, halogenated hydrocarbons such as dichloromethane, chloroform and 1,2-dichloroethane, ketone-type solvents such as acetone, polar organic solvents such as acetonitrile, N,N-dimethylformamide and dimethyl sulfoxide, water or mixed solvents thereof. Examples of the base include nitrogen-containing organic bases such as triethylamine, diisopropylethylamine and pyridine, inorganic bases such as potassium carbonate, sodium hydrogen carbonate, sodium hydroxide, sodium hydride and metallic sodium, organic bases such as sodium acetate, potassium acetate and ammonium acetate, alcoholates such as potassium t-butoxide and sodium ethoxide. The phase transfer catalyst may be exemplified by quaternary ammonium salts such as benzyltriethylammonium bromide, and crown ethers such as 18-crown-6-ether.

Step F

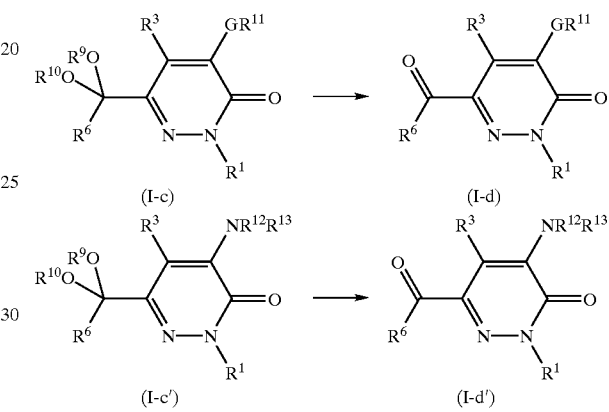

Step F

The compound (I-d or I-d') can be produced by reacting Compound (I-c or I-c') produced in Step E usually at room temperature to the boiling point of the solvent for 1 to 24 hours in an alcohol such as methanol or ethanol, an ether such as tetrahydrofuran or dioxane, water or a mixed solvent thereof in the presence of a mineral acid such as hydrochloric acid or sulfuric acid, an organic acid such as acetic acid or tartaric acid, perchloric acid, or the like.

Production Method 4

Step G

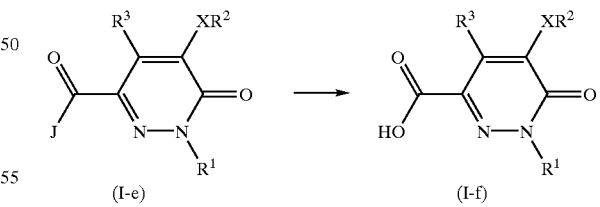

Step G

Compound (I-f) can be produced by hydrolyzing Compound (I-e) produced according to the method of Step B or C with a mineral acid such as hydrochloric acid or sulfuric acid, an organic acid such as formic acid, acetic acid or trifluoroacetic acid or an inorganic base such as potassium hydroxide or sodium hydroxide without solvent or in an alcohol such as methanol or ethanol, an ether such as tetrahydrofuran, diethyl ether or dioxane, a hydrocarbon such as toluene or benzene, a halogenated hydrocarbon such

Production Method 5

Step H

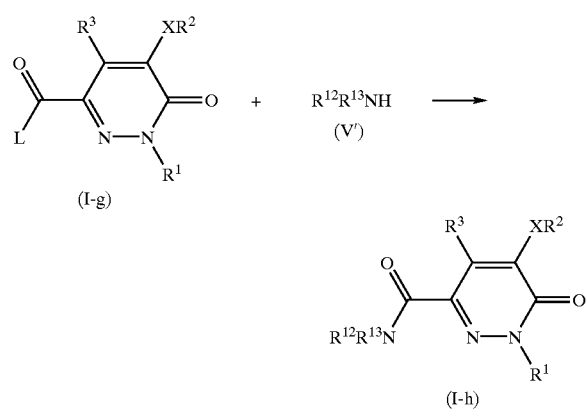

Step H

Compound (I-h) can be produced by reacting Compound (I-g) produced according to the method of Step B, C or G with an amine (V') without solvent or in an alcohol such as methanol or ethanol, an ether such as tetrahydrofuran, diethyl ether or dioxane, a hydrocarbon such as toluene or benzene, a halogenated hydrocarbon such as dichloromethane, chloroform or 1,2-dichloroethane, a polar organic solvent such as acetonitrile, N,N-dimethylformamide or dimethyl sulfoxide, water or a mixed solvent thereof in the presence or absence of a nitrogen-containing organic base such as pyridine or triethylamine or a dehydrating agent such as dicyclohexylcarbodiimide, usually at 0° C. to room temperature for 1 to 24 hours.

Production Method 6

Step I

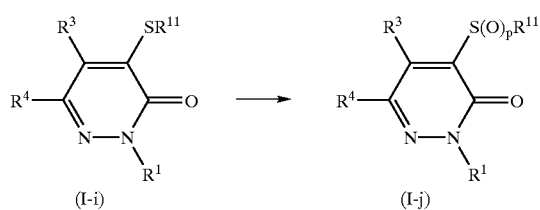

Step I

Compound (I-j) can be produced by reacting Compound (I-i) produced according to the method of Step B, C, E, F, G or H with 1 to 3 equivalents of an organic or inorganic oxidizing agent such as hydrogen peroxide, peracetic acid, m-chloroperbenzoic acid, potassium permanganate, N-chlorosuccinimide, chromic acid, potassium dichromate in a single solvent of a halogenated hydrocarbon such as dichloromethane, chloroform or 1,2-dichloroethane, an ether such as tetrahydrofuran, diethyl ether or dioxane, water, acetic acid, formic acid or the like, or a mixed solvent thereof, usually at 0° C. to 100° C. for 1 to 24 hours.

Production Method 7

Step J

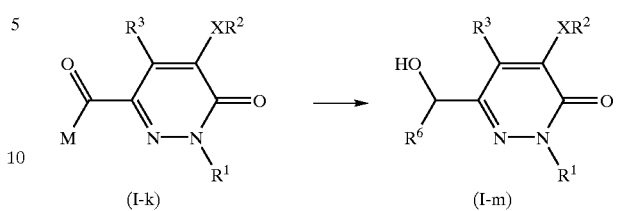

Step J

Compound (I-m) can be produced by reacting Compound (I-k) produced according to the method of Step B, C, F, G, H or I with a reducing agent, e.g., a metal hydride such as lithium aluminium hydride or sodium borohydride, a boron compound such as diborane, a silicon compound such as triethylsilane, or a tin compound such as tributyltin hydride in a single solvent of an alcohol such as methanol or ethanol, an ether such as dioxane, tetrahydrofuran or diethyl ether, a hydrocarbon such as toluene or benzene, water, acetic acid or the like, or a mixed solvent thereof, usually at 0° C. to room temperature for 1 to 24 hours.

Production Method 8

Step K

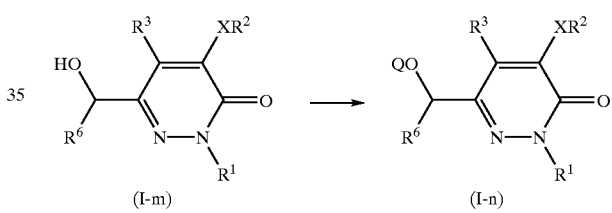

Step K

Compound (I-n) can be produced by reacting Compound (I-m) produced in Step I with an acyl halide or a carboxylic acid derivative of various type usually at 0° C. to room temperature for 1 to 24 hours in the presence or absence of an inert solvent and in the presence of a base or in the presence of a dehydrating agent such as dicyclohexylcarbodiimide using a phase transfer catalyst, if necessary. Examples of the inert solvent include ethers such as tetrahydrofuran, diethyl ether and dioxane, hydrocarbons such as toluene and benzene, halogenated hydrocarbons such as dichloromethane, chloroform and 1,2-dichloroethane, ketone-type solvents such as acetone, polar organic solvents such as acetonitrile, N,N-dimethylformamide and dimethyl sulfoxide as single solvents or mixed solvents thereof. Examples of the base include nitrogen-containing organic bases such as triethylamine, diisopropylethylamine and pyridine, inorganic bases such as potassium carbonate, sodium hydroxide, sodium hydride and metallic sodium, organic bases such as sodium acetate, potassium acetate and ammonium acetate, alcoholates such as potassium t-butoxide and sodium ethoxide. The phase transfer catalyst may be exemplified by quaternary ammonium salts such as benzyltriethylammonium bromide, and crown ethers such as 18-crown-6-ether.

Production Method 9

Step L

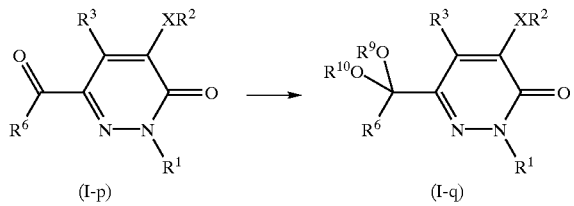

Step L

Compound (I-q) can be produced by reacting Compound (I-p) produced according to the method of Step B, C, D, F or I with an alcohol such as ethylene glycol usually at room temperature to the boiling point of the solvent for 1 to 48 hours under the usual conditions for protecting a carbonyl group, for example, in the presence of an organic acid catalyst such as p-toluenesulfonic acid in an aromatic hydrocarbon such as toluene or benzene with removing water formed in the reaction system by means of a water-separating apparatus, distillation, a Lewis acid such as boron trifluoride, or a dehydrating agent such as an orthoester.

Production Method 10

Step M

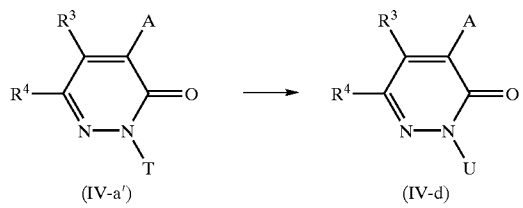

Compound (IV-d) can be produced by reacting Compound (IV-a') produced according to the method of Step A with 1 to 3 equivalents of an organic or inorganic oxidizing agent such as hydrogen peroxide, peracetic acid, m-chloroperbenzoic acid, potassium permanganate, N-chlorosuccinimide, chromic acid, potassium dichromate in a single solvent of a halogenated hydrocarbon such as dichloromethane, chloroform or 1,2-dichloroethane, an ether such as tetrahydrofuran, diethyl ether or dioxane, water, acetic acid, formic acid or the like, or a mixed solvent thereof, usually at 0° C. to 100° C. for 1 to 24 hours.

Step N

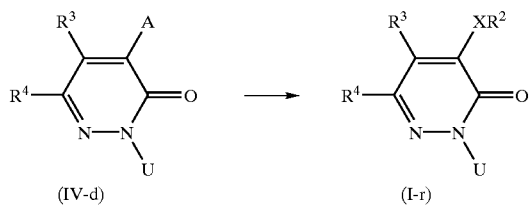

Step N

Compound (I-r) can be produced from Compound (IV-d) and Compound (V) according to the method of Step B.

Production Method 11

Step O

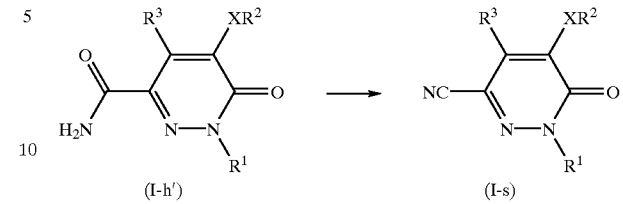

Step O

Compound (I-s) can be produced by reacting Compound (I-h') produced in Step H with a dehydrating agent such as acetic anhydride, acetic anhydride-sodium acetate, thionyl chloride, diphosphorus pentaoxide, phosphorus pentachloride, phosphorus oxychloride or dicyclohexylamide in the presence or absence of an inert solvent usually at room temperature to 30° C. for 1 to 24 hours. As the inert solvent, an ether such as tetrahydrofuran, diethyl ether or dioxane, an hydrocarbon such as toluene or benzene, a halogenated hydrocarbon such as dichloromethane, chloroform or 1,2-dichloroethane may be used singly or as a mixed solvent thereof.

Production Method 12

Step P

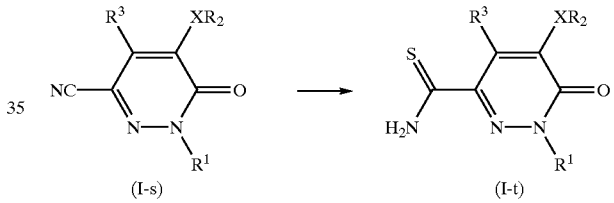

Step P

Compound (I-t) can be produced by reacting Compound (I-s) produced in Step O with hydrogen sulfide in the presence or absence of an inert solvent, optionally using a catalyst such as pyridine, pyridine-triethylamine or diethylamine, usually at 0° C. to room temperature for 1 to 24 hours. As the inert solvent, an ether such as tetrahydrofuran, diethyl ether or dioxane, a hydrocarbon such as toluene or benzene may be used singly or as a mixed solvent thereof.

Production Method 13

Step Q

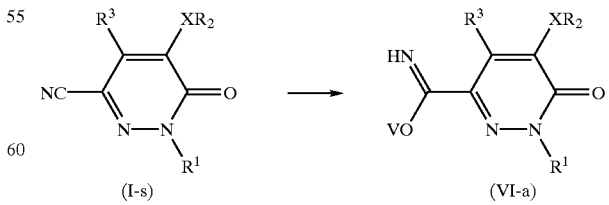

Step Q

Compound (VI-a) can be produced by reacting Compound (I-s) produced in Step O with an alcohol and hydrogen chloride usually at 0° C. to room temperature for 1 to 24 hours. Examples of the alcohol include methanol and ethanol.

Step R

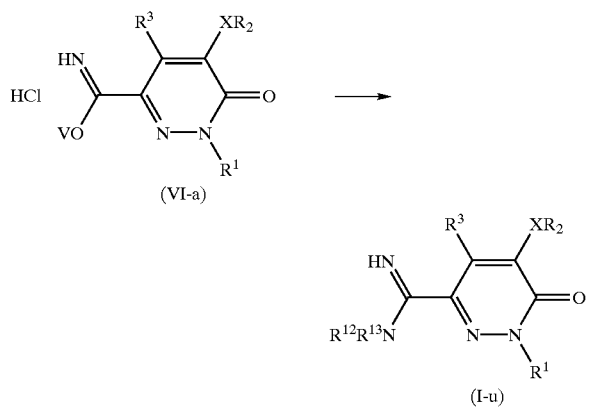

Step R

Compound (I-u) can be produced by reacting Compound (VI-a) produced in Step Q with an amine in an inert solvent such as an alcohol usually at room temperature to the boiling point of the solvent for 1 to 24 hours. Examples of the alcohol include methanol and ethanol.

The pyridazinone derivative represented by formula (I) or a pharmaceutically acceptable salt thereof according to the present invention is used solely or as a composition comprising a pharmaceutically acceptable inert carrier or diluent, with formulating it into a preparation form suitable for oral administration or parenteral administration, e.g., a liquid, a tablet (including a sugar-coated tablet, film-coated tablet), a powder, a granular, a capsule (including a soft capsule), an injection, a suspension, a suppository, an emulsion, an ointment, a cream, a lotion, a poultice or the like. The dose varies with age, body weight and administration form, but in the case of the treatment of the whole body, the compound may be generally administered in an amount of at least 0.05 mg/kg-body weight, preferably 0.5 to 10 mg/kg-body weight per adult by one dose or divided doses per day. In the case of topical treatment, e.g., a preparation for application, the concentration of the active ingredient may be at least 0.001%, preferably from 0.1 to 2% which is most suitable, and the preparation may be applied in an amount of 30 mg to 100 mg per cm$^2$. In the employment of the present inhibitor, it is also possible to use it as a mixture with other cell adhesion inhibitor.

EXAMPLES

The present invention will be explained below in detail with reference to Production Examples and Test Examples. However, the present invention is not limited thereto.

Production Example 1

Production of 6-acetyl-2-(4-chlorophenyl)-4-(4-chlorophenylthio)-5-methyl-3(2H)-pyridazinone (1) Pentan-2,3,4-trione 3-(4-chlorophenylhydrazone) (23.90 g) was added to a suspension of 66% sodium hydride (7.64 g) in anhydrous tetrahydrofuran (300 ml) under ice cooling, followed by stirring at room temperature for 30 minutes. Then, a solution of bromacetyl chloride (9.1 ml) in anhydrous tetrahydrofuran (100 ml) was added dropwise under ice cooling, followed by stirring at room temperature for 12 hours. The reaction mixture was poured into ice-water, and extracted with ethyl acetate. After washing with water and a brine, the organic layer was dried over anhydrous magnesium sulfate. The solvent was removed by evaporation, the resulting residue was purified by silica gel column chromatography (acetone:hexane=1:9), and crystallized from hexane to obtain 6-acetyl-4-bromo-2-(4-chlorophenyl)-5-methyl-3 (2H)-pyridazinone (11.96 g).

(2) To a solution of 97% sodium hydroxide (51 mg) in a mixture of water (3 ml) and N,N-dimethylformamide (10 ml) was added 4-chlorothiophenol (0.19 g), followed by stirring at room temperature for 30 minutes. Then, 6-acetyl-4-bromo-2-(4-chlorophenyl)-5-methyl-3(2H)-pyridazinone (0.30 g) was added, followed by stirring at room temperature for 1 hour. Water was added to the reaction mixture and the mixture was extracted with ethyl acetate. After washing with water and a brine, the organic layer was dried over anhydrous magnesium sulfate. The solvent was removed by evaporation, the resulting crude crystals were recrystallized from ethyl acetate/hexane to obtain 6-acetyl-2-(4-chlorophenyl)-4-(4-chlorophenylthio)-5-methyl-3(2H)-pyridazinone (260 mg) (Compound No. 1-29).

Production Example 2

Production of 6-acetyl-2-(3-chlorophenyl)-5-methyl-4-phenylthio-3(2H)-pyridazinone Pentan-2,3,4-trione 3-(3-chlorophenylhydrazone) (1.50 g) was added to a suspension of 66% sodium hydride (0.48 g) in anhydrous tetrahydrofuran (30 ml) under ice cooling, followed by stirring at room temperature for 30 minutes. Then, a solution of phenylthioacetyl chloride (1.19 g) in anhydrous tetrahydrofuran (5 ml) was added dropwise under ice cooling, followed by stirring at room temperature for 12 hours. The reaction mixture was poured into ice-water, and extracted with ethyl acetate. After washing with water and a brine, the organic layer was dried over anhydrous magnesium sulfate. The solvent was removed by evaporation, the resulting residue was purified by silica gel column chromatography (ethyl acetate:hexane=8:1), and the resulting crude crystals were recrystallized from ethyl acetate/hexane to obtain 6-acetyl-2-(3-chlorophenyl)-5-methyl-4-phenylthio-3(2H)-pyridazinone (1.6 g) (Compound No. 1-64).

Production Example 3

Production of methyl 1-(3-chlorophenyl)-5-(4-fluorophenylthio)-4-methyl-6-oxohydropyridazin-3-carboxylate (1) Pentan-2,3,4-trione 3-(3-chlorophenylhydrazone) (15.00 g) was added to a suspension of 66% sodium hydride (4.50 g) kin anhydrous tetrahydrofuran (180 ml) under ice cooling, followed by stirring at room temperature for 30 minutes. Then, a solution of bromacetyl chloride (5.4 ml) in anhydrous tetrahydrofuran (30 ml) was added dropwise under ice cooling, followed by stirring at room temperature for 12 hours. The reaction mixture was poured into ice-water, and extracted with ethyl acetate. After washing with water and a brine, the organic layer was dried over anhydrous magnesium sulfate. The solvent was removed by evaporation, and the resulting residue was purified by silica gel column chromatography (ethyl acetate:hexane= 1:3) to obtain methyl 5-bromo-1-(3-chlorophenyl)-4-methyl-6-oxohydropyridazin-3-carboxylate (4.10 g).

(2) To a suspension of 66% sodium hydride (0.11 g) in N,N-dimethylformamide (10 ml) was added 4-fluorothiophenol (0.48 ml), followed by stirring at room temperature for 30 minutes. Then, methyl 5-bromo-1-(3-chlorophenyl)-1,6-dihydro-4-methyl-6-oxopyridazinecarboxylate (1.07 g) was added, followed by stirring at room temperature for 1 hour. The reaction mixture was poured into water and the mixture was extracted with ethyl acetate. After washing with water and a brine, the organic layer was dried over anhydrous magnesium sulfate. The solvent was removed by evaporation, and the resulting crude crystals were recrystallized from ethyl acetate/hexane to obtain the aimed compound (0.75 g) (Compound No. 1-79).

Production Example 4

Production of 1-(3-chlorophenyl)-5-(4-fluorophenylthio)-methyl-6-oxohydropridazin-3-carboxylic acid A mixture of methyl 1-(3-chlorophenyl)-5-(4-fluorophenylthio)-4-methyl-6-oxohydropridazin-3-carboxylate (0.10 g), formic acid (1 ml) and sulfuric acid (1 ml) was heated under reflux for 3 hours. After cooling on standing, the reaction mixture was poured into water and extracted with ethyl acetate. After washing with water and a brine, the organic layer was dried over anhydrous magnesium sulfate. The solvent was removed by evaporation, and the resulting residue was purified by silica gel column chromatography (ethyl acetate:methanol=20:1) to obtain the aimed compound (0.05 g) (Compound No. 1-80).

Production Example 5

Production of 1-(3-chlorophenyl)-5-(4-fluorophenylthio)-4-methyl-6-oxohydropridazin-3-carboxamide To a solution of methyl 1-(3-chlorophenyl)-5-(4-fluorophenylthio)-4-methyl-6-oxohydropridazin-3-carboxylate (0.50 g) in ethanol (80 ml) were added 28% aqueous ammonia (30 ml) and ammonium chloride (0.07 g), followed by stirring at room temperature for 5 hours. The solvent was removed by evaporation, water was added to the resulting residue, and the mixture was extracted with ethyl acetate. After washing with water and a brine, the organic layer was dried over anhydrous magnesium sulfate. The solvent was removed by evaporation, and the resulting residue was purified by silica gel column chromatography (ethyl acetate:hexane=3:1) to obtain the aimed compound (0.35 g) (Compound No. 1-82).

Production Example 6

Production of 6-acetyl-2-(3-chlorophenyl)-5-methyl-4-phenylsulfonyl-3(2H)-pyridazinone To a solution of 6-acetyl-2-(3-chlorophenyl)-5-methyl-4-phenylthio-3(2H)-pyridazinone (0.37 g) in 1,2-dichloroethane (10 ml) was added m-chloroperbenzoic acid (0.65 g), followed by stirring at room temperature for 12 hours. An aqueous solution of sodium thiosulfate was added to the reaction mixture to decompose excess oxidizing agent, and then the mixture was extracted with chloroform. After washing with a saturated aqueous sodium hydrogen carbonate solution and a brine, the organic layer was dried over anhydrous magnesium sulfate. The solvent was removed by evaporation, and the resulting residue was allowed to stand at room temperature to obtain crystalline 6-acetyl-2-(3-chlorophenyl)-5-methyl-4-phenylsulfonyl-3(2H)-pyridazinone (0.38 g) (Compound No. 1-83).

Production Example 7

Production of 6-acetyl-2-(3-chlorophenyl)-5-methyl-4-(2-thienyl)-3(2H)-pyridazinone Pentan-2,3,4-trione 3-(3-chlorophenylhydrazone) (2.39 g) was added to a suspension of 66% sodium hydride (0.77 g) in anhydrous tetrahydrofuran (40 ml) under ice cooling, followed by stirring at room temperature for 30 minutes. Then, a solution of 2-thiopheneacetyl chloride (1.77 g) in anhydrous tetrahydrofuran (10 ml) was added dropwise under ice cooling, followed by stirring at room temperature for 2 hours. The reaction mixture was poured into water and extracted with ethyl acetate. After washing with water and a brine, the organic layer was dried over anhydrous magnesium sulfate. The solvent was removed by evaporation, the resulting residue was purified by silica gel column chromatography (ethyl acetate:hexane=1:4), and the resulting crude crystals were washed with hexane to obtain 6-acetyl-2-(3-chlorophenyl)-5-methyl-4-(2-thienyl)-3(2H)-pyridazinone (2.19 g) (Compound No. 1-97).

Production Example 8

Production of 6-acetyl-2-(4-fluorophenyl)-5-methyl-4-(3-pyridylmethoxy)-3(2H)-pyridazinone hydrochloride (1) A suspension of 6-acetyl-4-bromo-2-(4-fluorophenyl)-5-methyl-3(2H)-pyridazinone (3.2 g), ethylene glycol (3.1 g) and p-toluenesulfonic acid (0.2 g) in toluene (35 ml) was heated under reflux for 10 hours with removing water formed. After cooling on standing, the reaction mixture was extracted with ethyl acetate. After washing with a saturated aqueous sodium hydrogen carbonate solution and a brine, the organic layer was dried over anhydrous magnesium sulfate. The solvent was removed by evaporation, the resulting residue was purified by silica gel column chromatography (ethyl acetate:hexane=1:2), and the resulting crude crystals were washed with hexane to obtain 4-bromo-2-(4-fluorophenyl)-5-methyl-6-(2-methyl-1,3-dioxolan-2-yl)-3(2H)-pyridazinone (3.25 g).
(2) To a suspension of 62.5% sodium hydride (92 mg) in N,N-dimethylformamide (8 ml) was added 3-pyridylcarbinol (0.25 ml) under ice cooling, followed by stirring at room temperature for 20 minutes. Then, 4-bromo-2-(4-fluorophenyl)-5-methyl-6-(2-methyl-1,3-dioxolan-2-yl)-3(2H)-pyridazinone (738 mg) was added, followed by stirring at room temperature for 2 hours. The reaction mixture was poured into water and extracted with ethyl acetate. After washing with water and a brine, the organic layer was dried over anhydrous magnesium sulfate. The solvent was removed by evaporation, and the resulting residue was crystallized from ether to obtain 2-(4-fluorophenyl)-5-methyl-6-(2-methyl-1,3-dioxolan-2-yl)-4-(3-pyridylmethoxy)-3(2H)-pyridazinone (320 mg).
(3) To a solution of 2-(4-fluorophenyl)-5-methyl-6-(2-methyl-1,3-dioxolan-2-yl)-4-(3-pyridylmethoxy)-3(2H)-pyridazinone (320 mg) in N,N-tetrahydrofuran (12 ml) was added 6N hydrochloric acid (1.4 ml), followed by stirring at room temperature for 17 hours. The solvent was removed by evaporation, a saturated aqueous sodium hydrogen carbonate solution was added to the resulting residue to adjust the pH to about 10 and then the mixture was extracted with chloroform. After washing with water and a brine, the organic layer was dried over anhydrous magnesium sulfate. The solvent was removed by evaporation, and a 4M hydrogen chlorid/1,4-dioxane solution (10 ml) was added to the resulting residue, followed by stirring at room temperature for 10 minutes. The solvent was removed by evaporation, and the resulting residue was crystallized from ether to obtain 6-acetyl-2-(4-fluorophenyl)-5-methyl-4-(3-pyridylmethoxy)-3(2H)-pyridazinone hydrochloride (190 mg) (Compound No. 1-114).

Production Example 9

Production of 6-acetyl-2-(4-fluorophenyl)-5-methyl-4-((4-pyridyl N-oxide)methoxy)-3(2H)-pyridazinone (1) To, a solution of 2-(4-fluorophenyl)-5-methyl-6-(2-methyl-1,3-dioxolan-2-yl)-4-(4-pyridylmethoxy)-3(2H)-pyridazinone (400 mg) in 1,2-dichloroethane (10 ml) was added m-chloroperbenzoic acid (410 mg), followed by stirring at room temperature for 12 hours. An aqueous sodium thiosulfate solution was added to the reaction mixture to decompose excess oxidizing agent, and then the mixture was extracted with chloroform. After washing with a saturated aqueous sodium hydrogen carbonate solution and a brine, the organic layer was dried over anhydrous magnesium sulfate. The solvent was removed by evaporation, and the resulting crude crystals were washed with hexane to obtain 2-(4-fluorophenyl)-5-methyl-6-(2-methyl-1,3-dioxolan-2-yl)-4-((4-pyridyl N-oxide)methoxy)-3(2H)-pyridazinone (380 mg).

(2) To a solution of 2-(4-fluorophenyl)-5-methyl-6-(2-methyl-1,3-dioxolan-2-yl)-4-((4-pyridyl N-oxide)methoxy)-3(2H)-pyridazinone (380 mg) in tetrahydrofuran (12 ml) was added 6N hydrochloric acid (1.4 ml), followed by stirring at room temperature for 17 hours. The solvent was removed by evaporation, a saturated aqueous sodium hydrogen carbonate solution was added to the resulting residue to adjust the pH to about 10 and then the mixture was extracted with chloroform. After washing with water and a brine, the organic layer was dried over anhydrous magnesium sulfate. The solvent was removed by evaporation, and the resulting residue was crystallized from ether to obtain 6-acetyl-2-(4-fluorophenyl)-5-methyl-4-((4-pyridyl N-oxide)methoxy)-3(2H)-pyridazinone hydrochloride (250 mg) (Compound No. 1-130).

Production Example 10

Production of 6-acetyl-4-(4-fluorophenylthio)-5-methyl-2-(3-pyridyl N-oxide)-3(2H)-pyridazinone (1) To a solution of 6-acetyl-4-chloro-5-methyl-2-(3-pyridyl)-3(2H)-pyridazinone (1.0 g) in chloroform (20 ml) was added m-chloroperbenzoic acid (930 mg), followed by stirring at room temperature for 8 hours. An aqueous sodium thiosulfate solution was added to the reaction mixture to decompose excess oxidizing agent, and then the mixture was extracted with chloroform. After washing with a saturated aqueous sodium hydrogen carbonate solution and a brine, the organic layer was dried over anhydrous magnesium sulfate. The solvent was removed by evaporation, and the resulting crude crystals were washed with hexane to obtain 6-acetyl-4-chloro-5-methyl-2-(3-pyridyl N-oxide)-3(2H)-pyridazinone (590 mg).

(2) To a solution of 97% sodium hydroxide (45 mg) in a mixture of water (0.5 ml) and N,N-dimethylformamide (2.5 ml) was added 4-fluorothiophenol (180 mg), followed by stirring at room temperature for 30 minutes. Then, 6-acetyl-4-chloro-5-methyl-2-(3-pyridyl N-oxide)-3(2H)-pyridazinone (200 mg) was added, followed by stirring at room temperature for 1 hour. The reaction mixture was poured into water and extracted with ethyl acetate. After washing with water and a brine, the organic layer was dried over anhydrous magnesium sulfate. The solvent was removed by evaporation, and the resulting crude crystals were recrystallized from ethyl acetate/hexane to obtain 6-acetyl-4-(4-fluorophenylthio)-5-methyl-2-(3-pyridyl N-oxide)-3(2H)-pyridazinone (220 mg) (Compound No. 1-134).

Production Example 11

Production of 6-acetyl-4-(aminothioxomethyl)-2-(3-chlorophenyl)-5-methyl-3(2H)-pyridazinone Hydrogen sulfide was bubbled into a solution of 6-acetyl-2-(3-chlorophenyl)-5-methyl-3-oxo-2-hydropyridazin-4-carbonitrile (1.36 g) and triethylamine (0.8 ml) in pyridine (20 ml) at 10° C. for 10 minutes, followed by stirring at the same temperature for 1 hour. The solvent was removed by evaporation, and the resulting residue was crystallized from ethyl acetate/hexane to obtain 6-acetyl-4-(aminothioxomethyl)-2-(3-chlorophenyl)-5-methyl-3(2H)-pyridazinone (0.90 g) (Compound No. 1-153).

Production-Example 12

Production of 6-acetyl-2-(3-chlorophenyl )-5-methyl-4-(1,3-thiazol-2yl)-3(2H)-pyridazinone To a suspension (5 ml) of 6-acetyl-4-(aminothioxomethyl)-2-(3-chlorophenyl)-5-methyl-3(2H)-pyridazinone (200 mg) in ethanol (5 ml) was added a 50% aqueous solution of chloroacetoaldehyde, followed by heating under reflux for 10 hours. After cooling on standing, the reaction mixture was extracted with ethyl acetate. After washing with a saturated sodium hydrogen carbonate aqueous solution and a brine, the organic layer was dried over anhydrous magnesium sulfate. The solvent was removed by evaporation, the resulting residue was purified by silica gel column chromatography (ethyl acetate:hexane=1:2), and the resulting crude crystals was washed with hexane to obtain 6-acetyl-2-(3-chlorophenyl)-5-methyl-4-(1,3-thiazol-2-yl)-3(2H)-pyridazinone (90 mg) (Compound No. 1-155).

Production Example 13

Production of 4-((6-acetyl-2-(4-fluorophenyl)-5-methyl-3-oxo-2-hydropyridazin-4-yloxy)methyl)pyridin-2-carbonitrile (1) A solution (2 ml) of 2-(4-fluorophenyl)-5-methyl-6-(2-methyl-1,3-dioxolan-2-yl)-4-((4-pyridyl N-oxide)methoxy)-3(2H)-pyridazinone (200 mg) and trimethylsilylnitrile (53 mg) in 1,2-dichloromethane (2 ml) was stirred at room temperature for 5 minutes. Then, N,N-dimethylcarbamyl chloride (51 mg) was added, followed by stirring at the same temperature for 24 hours. A 10% aqueous potassium carbonate solution was added to the reaction mixture, followed by stirring for 10 minutes, and then the mixture was extracted with chloroform. After the organic layer was dried over anhydrous magnesium sulfate, the solvent was removed by evaporation, the resulting residue was purified by silica gel column chromatography (ethyl acetate:hexane=1:1), and the resulting crude crystals was washed with hexane to obtain 4-((2-(4-fluorophenyl)-5-methyl-6-(2-methyl-1,3-dioxolan-2-yl)-3-oxo-2-hydropyridazin-4-yloxy)methyl)pyridin-2-carbonitrile (106 mg).

(2) To a solution of 4-((2-(4-fluorophenyl)-5-methyl-6-(2-methyl-1,3-dioxolan-2-yl)-3-oxo-2-hydropyridazin-4-yloxy)methyl)pyridin-2-carbonitrile (100 mg) in tetrahydrofuran (3 ml) was added 4N hydrochloric acid (0.6 ml), followed by stirring at room temperature for 24 ours. The solvent was removed by evaporation, a saturated aqueous sodium hydrogen carbonate solution was added to the resulting residue to adjust the pH to about 10 and then the mixture was extracted with chloroform. After washing with water and a brine, the organic layer was dried over anhydrous magnesium sulfate. The solvent was removed by evaporation, and the resulting residue was crystallized from ether to obtain 4-((6-acetyl-2-(4-fluorophenyl)-5-methyl-3-oxo-2-hydropyridazin-4-yloxy)methyl)pyridin-2-carbonitrile (65 mg) (Compound No. 1-163).

Production Example 14

Production of 4-((6-acetyl-2-(4-fluorophenyl)-5-methyl-3-oxo-2-hydropyridazin-4-yloxy)methyl) pyridin-2-carboxylic acid To a solution of 4-((6-acetyl-2-(4-fluorophenyl)-5-methyl-3-oxo-2-hydropyridazin-4-yloxy)methyl)pyridin-2-carbonitrile (100 mg) in 1,4-dioxane (5 ml) was added 6N hydrochloric acid (3 ml), followed by heating under reflux for 24 hours. The solvent was removed by evaporation, a 10% aqueous sodium hydroxide solution was added to the resulting residue to adjust the pH to 3 to 4, and then the mixture was stirred at room temperature for 1 hour. The crystals precipitated were filtered off, washed with water and diethyl ether, and then dried to obtain 4-((6-acetyl-2-(4-fluorophenyl)-5-methyl-3-oxo-2-hydropyridazin-4-yloxy) methyl)pyridin-2-carboxylic acid (53 mg) (Compound No. 1-164).

Production Example 15

Production of 6-acetyl-2-(4-fluorophenyl)-5-methyl-4-(4-methylsulfonylaminophenylthio)-3(2H)-pyridazinone Methanesulfonyl chloride (0.1 ml) was added to a solution of 6-acetyl-4-(4-aminophenylthio)-2-(4-fluorophenyl)-5-methyl-3(2H)-pyridazinone (185 mg) in pyridine (2 ml) at 5° C., followed by stirring at room temperature for 1 hour. Water was added to the reaction mixture and the mixture was extracted with ethyl acetate. After washing with a saturated aqueous sodium hydrogen carbonate solution and a brine, the organic layer was dried over anhydrous magnesium sulfate. The solvent was removed by evaporation, and the resulting residue was purified by silica gel column chromatography (ethyl acetate:hexane=1:1), and was crystallized from ether to obtain 6-acetyl-2-(4-fluorophenyl)-5-methyl-4-(4-methylsulfonylaminophenylthio)-3(2H)-pyridazinone (180 mg) (Compound No. 4-01).

Production Example 16

Production of 6-acetyl-4-(4-dimethylaminophenylthio)-2-(4-fluorophenyl)-5-methyl-3(2H)-pyridazinone Methyl iodide (0.9 ml) was added to a solution of 6-acetyl-4-(4-aminophenylthio)-2-(4-fluorophenyl)-5-methyl-3(2H)-pyridazinone (370 mg) and 2,6-lutidine (1 ml) in N,N-dimethylformamide (5 ml) at 5° C., followed by stirring at room temperature for 12 hours. Water was added to the reaction mixture and the mixture was extracted with ethyl acetate. After washing with water and a brine, the organic layer was dried over anhydrous magnesium sulfate. The solvent was removed by evaporation, and the resulting residue was purified by silica gel column chromatography (ethyl acetate:hexane=1:1), and was crystallized from ether/hexane to obtain 6-acetyl-4-(4-dimethylaminophenylthio)-2-(4-fluorophenyl)-5-methyl-3(2H)-pyridazinone (120 mg) (Compound No. 4-04).

Production Example 17

Production of 6-acetyl-2-(4-fluorophenyl)-5-methyl-4-(2-morpholin-4-ylethylthio)-3(2H)-pyridazinone (1) Triethylamine (1.20 g) and methanesulfonyl chloride (1.24 g) were added to a solution of 6-acetyl-2-(4-fluorophenyl)-4-(2-hydroxyethylthio)-5-methyl-3(2H)-pyridazinone (2.90 g) in 1,2-dichloromethane (30 ml) under ice cooling, followed by stirring at room temperature for 30 minutes. Water was added to the reaction mixture and the mixture was extracted with chloroform. After washing with water and a brine, the organic layer was dried over anhydrous magnesium sulfate. The solvent was removed by evaporation, and the resulting residue was crystallized from ether/hexane to obtain 2-(6-acetyl-2-(4-fluorophenyl)-5-methyl-3-oxo-2-hydropyridazin-4-ylthio)ethyl methylsulfonate (3.18 g).

(2) A solution of 2-(6-acetyl-2-(4-fluorophenyl)-5-methyl-3-oxo-2-hydropyridazin-4-ylthio)ethyl methylsulfonate (400 mg) and morpholine (870 mg) in 1,2-dichloromethane (4 ml) was stirred at room temperature for 20 hours. Water was added to the reaction mixture and the mixture was extracted with chloroform. After washing with water and a brine, the organic layer was dried over anhydrous magnesium sulfate. The solvent was removed by evaporation, and the resulting residue was purified by silica gel column chromatography (ethyl acetate:hexane= 2:1), and was crystallized from hexane to obtain 6-acetyl-2-(4-fluorophenyl)-5-methyl-4-(2-morpholin-4-ylethylthio)-3(2H)-pyridazinone (145 mg) (Compound No. 5-04).

Production Example 18

Production of 2-(3-chlorophenyl)-6-(1-hydroxyethyl)-5-methyl-4-phenylthio-3(2H)-pyridazinone Sodium borohydride (26 mg) was added to a solution of 6-acetyl-2-(4-chlorophenyl)-4-(4-chlorophenylthio)-5-methyl-3(2H)-pyridazinone (0.50 g) in ethanol (50 ml) under ice cooling, followed by stirring at 5° C. for 3 hours. The reaction mixture was poured into water and extracted with chloroform. After washing with water and a brine, the organic layer was dried over anhydrous magnesium sulfate. The solvent was removed by evaporation, and the resulting residue was allowed to stand at room temperature to obtain crystalline 2-(3-chlorophenyl)-6-(1-hydroxyethyl)-5-methyl-4-phenylthio-3(2H)-pyridazinone (0.48 g) (Compound No. 6-01).

Formula (I)

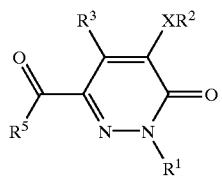

(I)

TABLE 1

| Compound No. | $R^1$ | X | $R^2$ | $R^3$ | $R^5$ | Melting point (° C.) |
|---|---|---|---|---|---|---|
| 1-01 | 3—Cl—Ph | S | 2—Cl—Ph | Me | Me | 136–137 |
| 1-02 | 3-Cl—Ph | S | 3-Cl—Ph | Me | Me | 120–121 |
| 1-03 | 3-Cl—Ph | S | 4-Cl—Ph | Me | Me | 135–136 |
| 1-04 | 3-Cl—Ph | S | 2-MeO—Ph | Me | Me | 115–116 |
| 1-05 | 3-Cl—Ph | S | 3-MeO—Ph | Me | Me | 76–77 |
| 1-06 | 3-Cl—Ph | S | 4-MeO—Ph | Me | Me | 60–62 |
| 1-07 | 3-Cl—Ph | S | 4-F—Ph | Me | Me | 95–96 |
| 1-08 | 3-Cl—Ph | S | 4-Me—Ph | Me | Me | 102–103 |
| 1-09 | 3-Cl—Ph | S | 4-tBu—Ph | Me | Me | 104–105 |
| 1-10 | 3-Cl—Ph | S | 4-NO$_2$—Ph | Me | Me | 158–160 |
| 1-11 | 3-Cl—Ph | S | 2-pyridyl | Me | Me | 119–120 |
| 1-12 | 3-Cl—Ph | S | 2-pyridyl | Me | Me | 159–160 |
| 1-13 | 3-Cl—Ph | S | 2-pyrimidinyl | Me | Me | 124–125 |
| 1-14 | 3-Cl—Ph | S | 4-Me-3-(4H-1,2,4-triazolyl) | Me | Me | 157–156 |
| 1-15 | 3-Cl—Ph | S | Me | Me | Me | 130–132 |
| 1-16 | 3-Cl—Ph | S | iPr | Me | Me | 69–71 |
| 1-17 | 3-Cl—Ph | S | tBu | Me | Me | 51–53 |
| 1-16 | 4-MeO—Ph | S | Et | Me | Me | 110–112 |
| 1-19 | 3-Cl—Ph | S | Bn | Me | Me | 97–99 |
| 1-20 | 4-F—Ph | S | 4-F—Ph | Me | Me | 111–112 |
| 1-21 | 4-F—Ph | S | 2-pyridyl | Me | Me | 126–129 |
| 1-22 | 4-F—Ph | S | 3-pyridyl | Me | Me | 116–117 |
| 1-23 | 4-F—Ph | S | 3-pyridyl | Me | Me | 157–159 (hydrochloride) |
| 1-24 | 4-F—Ph | S | 4-pyridyl | Me | Me | 132–133 |
| 1-25 | 4-F—Ph | S | 4-pyridyl | Me | Me | 109–115 (hydrochloride) |
| 1-26 | 3-Cl—Ph | S | CH$_2$CO$_2$Me | Me | Me | 130–131 |
| 1-27 | 4-F—Ph | S | CH$_2$CO$_2$Me | Me | Me | 129–130 |
| 1-26 | 4-F—Ph | S | CH$_2$CH$_2$CO$_2$Et | Me | Me | 47–46 |
| 1-29 | 4-Cl—Ph | S | 4-Cl—Ph | Me | Me | 165–166 |
| 1-30 | 4-MeO—Ph | S | Ph | Me | Me | 90–92 |
| 1-31 | 3-pyridyl | S | 4-F—Ph | Me | Me | 61–83 |
| 1-32 | 3-pyridyl | S | 4-pyridyl | Me | Me | 148–149 |
| 1-33 | 3-pyridyl | O | Et | Me | Me | 146–149 |
| 1-34 | 4-F—Ph | S | CH$_2$CH$_2$NMe$_2$ | Me | Me | 186–190 (hydrochloride) |
| 1-35 | 4-F—Ph | S | CH$_2$CH$_2$NMe$_2$ | Me | Me | 49–51 |
| 1-36 | 4-F—Ph | S | 2-imidazolyl | Me | Me | 225–227 |
| 1-37 | 4-F—Ph | S | 2-thiazolyl | Me | Me | 101–102 |
| 1-38 | 4-F—Ph | S | CHCH$_2$OH | Me | Me | 122–123 |
| 1-39 | 4-F—Ph | S | CH$_2$CH$_2$NHAC | Me | Me | 133–134 |
| 1-40 | 4-F—Ph | S | 5-HO$_2$C-2-pyridyl | Me | Me | 230–232 |
| 1-41 | 4-F—Ph | S | 3-HO$_2$C-2-pyridyl | Me | Me | 226–228 |
| 1-42 | 4-F—Ph | S | 4-OH—3,5-di-tBu—Ph | Me | Me | 119–120 |
| 1-43 | 4-F—Ph | S | 2-HO$_2$C—Ph | Me | Me | 238–239 |
| 1-44 | 4-F—Ph | S | 3-(1H—1,2,4-triazolyl) | Me | Me | 180–182 |
| 1-45 | 4-F—Ph | S | 1-Me—5—(1H—tetrazolyl) | Me | Me | 91–93 |
| 1-46 | 4-F—Ph | S | 5-Me—2-(1,3,4-thiadiazolyl) | Me | Me | 84–B6 |
| 1-47 | 4-F—Ph | S | 8-quinolyl | Me | Me | 101–103 |
| 1-48 | 4-F—Ph | S | 2-thienyl | Me | Me | 67–69 |
| 1-49 | 2-CN—Ph | S | 4-F—Ph | Me | Me | 118–120 |
| 1-50 | 6-MeO—3-pyridyl | S | 4-F—Ph | Me | Me | 88–89 |
| 1-51 | 4-F—Ph | S | CH$_2$CH$_2$NH$_2$ | Me | Me | 104–106 |
| 1-52 | 3-pyridyl | S | 4-NH$_2$—Ph | Me | Me | 161–163 |
| 1-53 | 3-pyridyl | S | 2-NH$_2$—Ph | Me | Me | 146–150 |
| 1-54 | 4-F—Ph | S | 2-NH$_2$—Ph | Me | Me | 140–142 |
| 1-55 | 4-F—Ph | S | 3-NH$_2$—Ph | Me | Me | 132–134 |
| 1-56 | 4-F—Ph | S | 4-NH$_2$—Ph | Me | Me | 148–150 |
| 1-57 | 4-F—Ph | S | 4-NH$_2$—Ph | Me | Me | 169–174 (hydrochloride) |
| 1-56 | 4-F—Ph | S | 4-AcNH—Ph | Me | Me | 210–212 |
| 1-59 | 3-pyridyl | S | 4-AcNH—Ph | Me | Me | 181–183 |
| 1-60 | 3-pyridyl | S | CH$_2$CH$_2$NH$_2$ | Me | Me | 112–114 |
| 1-61 | 3-Cl—Ph | S | CH$_2$CH$_2$NH$_2$ | Me | Me | 64–86 |
| 1-62 | 4-F—Ph | S | (CH$_2$)$_3$OH | Me | Me | 97–96 |
| 1-63 | 3-Cl—Ph | S | 2-pyridyl N—oxide | Me | Me | 165–166 |
| 1-64 | 3-Cl—Ph | S | Ph | Me | Me | 99–100 |
| 1-65 | 3-Cl—Ph | S | Ph | H | Me | 142–144 |
| 1-66 | 3,4-Cl—Ph | S | Ph | Me | Me | 122–127 |
| 1-67 | 2-Cl—Ph | S | Ph | Me | Me | 77–78 |
| 1-68 | 3-pyridyl | S | Ph | Me | Me | 63–64 |
| 1-69 | 4-F—Ph | S | Ph | Me | Me | 121–122 |
| 1-70 | 3-Cl—Ph | O | Ph | Me | Me | 139–141 |
| 1-71 | 3-Cl—Ph | O | 4-Cl—Ph | Me | Me | 166–167 |
| 1-72 | 4-Cl—Ph | O | 4-Cl—Ph | Me | Me | 169–170 |
| 1-73 | 3-Cl—Ph | O | 4-F—Ph | Me | Me | 147–146 |
| 1-74 | 3-F—Ph | O | 4-F—Ph | Me | Me | 165–166 |
| 1-75 | 3-Cl—Ph | 13 | CN | Me | Me | 139–141 |
| 1-76 | C—Cl—Ph | S | Ph | Ph | Me | 198–199 |
| 1-77 | 4-F—Ph | — | CO$_2$Et | Me | Me | 96–97 |
| 1-78 | 3-Cl—Ph | S | Ph | Me | OMe | 55–57 |
| 1-79 | 3-Cl—Ph | S | 4-F—Ph | Me | OMe | 113–115 |
| 1-80 | 3-Cl—Ph | S | 4-F—Ph | Me | OH | 215–225 |
| 1-81 | 3-Cl—Ph | S | Ph | Me | NH$_2$ | 87–89 |
| 1-81 | 3-Cl—Ph | S | 4-F—Ph | Me | NH$_2$ | 126–128 |
| 1-83 | 3-Cl—Ph | SO$_2$ | Ph | Me | Me | 175–176 |
| 1-84 | 3-Cl—Ph | SO | Ph | Me | Me | 186–188 |
| 1-85 | 4-F—Ph | SO$_2$ | 4-pyridyl | Me | Me | 206–206 |
| 1-86 | 3-pyridyl N—oxide | SO | 4—F-Ph | Me | Me | 161–163 |
| 1-87 | 4-F—Ph | S | 4-F—Ph | H | NH$_2$ | 71–73 |
| 1-88 | 4-F—Ph | S | 4-F—Ph | Me | OH | 203–204 |
| 1-89 | 4-F—Ph | S | 4-F—Ph | Me | OMe | 106–10B |
| 1-90 | 4-F—Ph | S | 4-AcNH—Ph | Me | OMe | 147–148 |
| 1-91 | 4-F—Ph | S | 4-AcNH—Ph | Me | OH | 213–215 |
| 1-92 | 4-F—Ph | S | 4-AcNH—Ph | Me | OH | 260 (decomposed, hydrochloride) |
| 1-93 | 4-F—Ph | S | 4-F—Ph | Me | NH-OH | 145–147 |
| 1-94 | 4-F—Ph | S | 4-NH$_2$—Ph | Me | OMe | 126–129 |
| 1-95 | 4-F—Ph | S | 4-AcNH—Ph | Me | NH$_2$ | 237–236 |
| 1-96 | 4-F—Ph | S | 4-NH$_2$—Ph | Me | NH$_2$ | 166–169 |
| 1-97 | 3-Cl—Ph | — | 2-thienyl | Me | Me | 116–117 |
| 1-96 | 3-F—Ph | — | 2-thienyl | Me | Me | 112–113 |
| 1-99 | 4-MeO—Ph | — | 2-thienyl | Me | Me | 122–123 |
| 1-100 | 4-F—Ph | — | 2-thienyl | Me | Me | 130–131 |
| 1-101 | 4-F—Ph | — | 3-thienyl | Me | Me | 96–97 |
| 1-102 | 3-pyridyl | — | 2-thienyl | Me | Me | 69–90 |
| 1-103 | 3-Cl—Ph | — | Ph | Me | Me | 94–95 |
| 1-104 | 3-Cl—Ph | — | 2-MeO—Ph | Me | Me | 100–102 |
| 1-105 | 3-Cl—Ph | — | 4-MeO—Ph | Me | Me | 102–104 |

TABLE 1-continued

| Compound No. | R¹ | X | R² | R³ | R⁵ | Melting point (° C.) |
|---|---|---|---|---|---|---|
| 1-106 | 3-Cl—Ph | — | 3,4-(MeO)₂—Ph | Me | Me | 132–134 |
| 1-107 | 4-F—Ph | O | i-Pr | Me | Me | 79–60 |
| 1-108 | 4-F—Ph | O | cyclopentyl | Me | Me | 95–96 |
| 1-109 | 4-F—Ph | O | CH₂CH₂NMe₂ | Me | Me | 175–176 (hydrochloride) |
| 1-110 | 4-F—Ph | O | 3-pyridyl | Me | Me | 165–166 |
| 1-111 | 4-F—Ph | O | 4-pyridyl | Me | Me | 164–165 |
| 1-112 | 4-F—Ph | O | 1-methyl—4-piperidino | Me | Me | 163–164 (hydrochloride) |
| 1-113 | 4-F—Ph | O | 2-pyridylmethyl | Me | Me | 153–154 |
| 1-114 | 4-F—Ph | O | 3-pyridylmethyl | Me | Me | 153–156 (hydrochloride) |
| 1-115 | 4-F—Ph | O | 4-pyridylmethyl | Me | Me | 167–168 |
| 1-116 | 4-F—Ph | O | 4—F—benzyl | Me | Me | 168–169 |
| 1-117 | 4-F—Ph | O | 2—thienylmethyl | Me | Me | 146–147 |
| 1-118 | 4-F—Ph | O | 3—thienylmethyl | Me | Me | 153–154 |
| 1-119 | 4-F—Ph | O | 2—furylmethyl | Me | Me | 145–146 |
| 1-120 | 4-F—Ph | O | 3—furylmethyl | Me | Me | 153–154 |
| 1-121 | 4-F—Ph | O | 2—thiazolylmethyl | Me | Me | 172–173 |
| 1-122 | 4-F—Ph | O | (4—methyl—5-thiazolyl)ethyl | Me | Me | 79–60 |
| 1-123 | 4-F—Ph | O | 2—thienylethyl | Me | Me | 67–68 |
| 1-124 | 4-F—Ph | O | 3—thienylethyl | Me | Me | 65–66 |
| 1-125 | 4-F—Ph | O | (4—Cl—2—pyridyl)methyl | Me | Me | 155–156 |
| 1-126 | 3-pyridyl N-oxide | O | 4—pyridylmethyl | Me | Me | 161–162 |
| 1-127 | 3-pyridyl N-oxide | O | 4—F—Ph | Me | Me | 171–173 |
| 1-128 | 4-F—Ph | O | 2—pyridylmethyl N-oxide | Me | Me | 218–220 |
| 1-129 | 4-F—Ph | O | 3—pyridylmethyl N-oxide | Me | Me | 186–186 |
| 1-130 | 4-F—Ph | O | 4—pyridylmethyl N-oxide | Me | Me | 165–167 |
| 1-131 | 4-F—Ph | O | (4-Cl-2-pyridyl)methyl N-oxide | Me | Me | 136–139 |
| 1-132 | 4-F—Ph | O | 3-pyridyl N-oxide | Me | Me | 182–184 |
| 1-133 | 4-F—Ph | O | (6-Me-2-pyridyl)methyl N-oxide | Me | Me | 175–177 |
| 1-134 | 3-pyridyl N-oxide | S | 4-F—Ph | Me | Me | 122–123 |
| 1-135 | 3-pyridyl N-oxide | S | 4-Cl—Ph | Me | Me | 172–174 |
| 1-136 | 3-pyridyl N-oxide | S | 2,4-di-F—Ph | Me | Me | 152–154 |
| 1-137 | 3-pyridyl N-oxide | S | 4-Me—Ph | Me | Me | 176–176 |
| 1-138 | 3-pyridyl N-oxide | S | 2-OMe—Ph | Me | Me | paste* |
| 1-139 | 3-pyridyl N-oxide | S | 3-OMe—Ph | Me | Me | 85–87 |
| 1-140 | 3-pyridyl N-oxide | S | 4-OMe—Ph | Me | Me | 166–166 |
| 1-141 | 3-pyridyl N-oxide | S | 3,4-di-OMe—Ph | Me | Me | 106–108 |
| 1-142 | 3-pyridyl N-oxide | S | 4-OCF₃—Ph | Me | Me | 182–184 |
| 1-143 | 3-pyridyl N-oxide | S | Et | Me | Me | 150–152 |
| 1-144 | 3-pyridyl N-oxide | S | i-Pr | Me | Me | 108–110 |
| 1-145 | 6-OMe—3—pyridyl N-oxide | S | 4-F—Ph | Me | Me | 120–122 |
| 1-146 | 3-pyridyl N-oxide | S | 2-thienyl | Me | Me | paste* |
| 1-147 | 3-pyridyl N-oxide | S | 4-pyridyl | Me | Me | 147–149 |
| 1-148 | 3-pyridyl N-oxide | S | 4-OMe—Bn | Me | Me | 53–155 |
| 1-149 | 3-pyridyl N-oxide | S | CH₂CO₂Et | Me | Me | 107–109 |
| 1-150 | 3-pyridyl N-oxide | S | 4-NH₂—Ph | Me | Me | 167–189 |
| 1-151 | 3-pyridyl N-oxide | S | 4-NHAc—Ph | Me | Me | 243–245 |
| 1-152 | 3-pyridyl N-oxide | S | CH₂CH₂NH₂ | Me | Me | 166–168 |
| 1-153 | 3-Cl—Ph | — | CSNH₂ | Me | Me | 195–197 |
| 1-154 | 3-Cl—Ph | — | 4-CO₂Et-2-thienyl | Me | Me | 172–174 |
| 1-155 | 3-Cl—Ph | — | 2-thiazolyl | Me | Me | 158–160 |
| 1-156 | 3-Cl—Ph | — | 4-CO₂H-2-thienyl | Me | Me | 264–266 |
| 1-157 | 3-Cl—Ph | S | CH₂CO₂H | Me | Me | 159–160 |
| 1-158 | 4-F—Ph | S | CH₂CO₂H | Me | Me | 158–160 |
| 1-159 | 4-F—Ph | S | CH₂CH₂CO₂H | Me | Me | 103–105 |
| 1-160 | 4-F—Ph | S | CH₂CONH₂ | Me | Me | 168–170 |
| 1-161 | 4-F—Ph | O | CH₂CO₂H | Me | Me | 177–178 |
| 1-162 | 4-F—Ph | — | CO₂H | Me | Me | 127–128 |
| 1-163 | 4-F—Ph | O | (2-CN-4-pyridyl)methyl | Me | Me | 166–167 |
| 1-164 | 4-F—Ph | O | (2-CO₂H-4-pyridyl)methyl | Me | Me | 217 (decomposed) |
| 1-165 | 2-CN-3-pyridyl | S | 4-F—Ph | Me | Me | 96–97 |
| 1-166 | 6-CN—3—pyridyl | S | 4-F—Ph | Me | Me | 101–101 |
| 1-167 | 3-Cl—Ph | S | 2-thienyl | Me | Me | 106–107 |
| 1-168 | 3-Cl—Ph | S | 3-pyridyl | Me | Me | 136–136 |
| 1-169 | 3-Cl—Ph | S | 4-NH₂—Ph | Me | Me | 125–126 |
| 1-170 | 3-Cl—Ph | S | 4-NHAc—Ph | Me | Me | 202–204 |
| 1-171 | 3-Cl—Ph | S | (CH₂)₂OH | Me | Me | 107–108 |
| 1-172 | 3-Cl—Ph | S | (CH₂)₃OH | Me | Me | 77–79 |
| 1-173 | 3-Cl—Ph | S | 1-methyl—5-(1H—tetrazolyl) | Me | Me | 81–83 |
| 1-174 | 3-Cl—Ph | S | 2-F—Ph | Me | OBu-t | 96–97 |

NMR data of the compounds having a paste property in Table 1 are shown below.

| Compound No. | ¹H—NMR (CDCl₃/TMS, δ value (ppm))* |
|---|---|
| 1-138 | 2.61 (3H, s), 2.65 (3H, s), 3.83 (3H, s), 6.87–6.90 (2H m), 7.26–7.34 (3H, m), 7.75 (1H, d, 8.4 Hz), 8.19 (1H, d, 6.5 Hz), 8.65 (1H, s) |
| 1-146 | 2.59 (3H, s), 2.75 (3H, s), 7.00 (1H, dd, 3.7 Hz, 5.1 Hz), 7.34–7.41 (3H, m), 7.75 (1 H, d, 8.5 Hz), 8.22 (1H, d, 6.2 Hz), 8.65 (1H, s) |

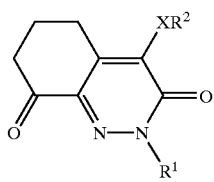

TABLE 2

| Compound No. | $R^1$ | X | $R^2$ | Melting point (° C.) |
|---|---|---|---|---|
| 2-01 | 4-F—Ph | S | Ph | 212–213 |

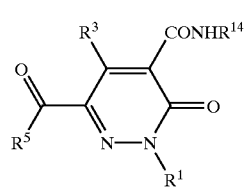

TABLE 3

| Compound No. | $R^1$ | X | $R^{14}$ | $R^3$ | $R^5$ | Melting point (° C.) |
|---|---|---|---|---|---|---|
| 3-01 | 4-F—Ph | — | 3—pyridyl | Me | Me | amorphous* |
| 3-02 | 4-F—Ph | — | $CH_2CO_2Et$ | Me | Me | 105–106 |
| 3-03 | 3-Cl—Ph | — | H | Me | Me | 141–142 |

NMR data of compound 3-01 are shown below.

| Compound No. | $^1$H-NMR (CDCl$_3$/TMS, δ value (ppm)) |
|---|---|
| 3-01 | 2.58 (3H, s), 2.73 (3H, s), 7.17–7.28 (3H, m), 7.56 (2H, m), 8.21 (1H, m), 8.31 (1H, m), 8.65 (1H, s) |

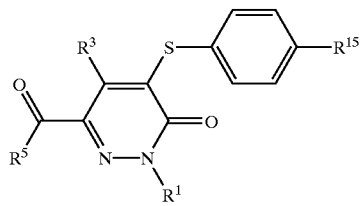

TABLE 4

| Compound No. | $R^1$ | X | $R^{15}$ | $R^3$ | $R^5$ | Melting point (° C.) |
|---|---|---|---|---|---|---|
| 4-01 | 4-F—Ph | S | $NHSO_2Me$ | Me | Me | 182–184 |
| 4-02 | 4-F—Ph | S | $NHSO_2Ph$ | Me | Me | 258–260 |
| 4-03 | 3-pyridyl | S | $NHSO_2Me$ | Me | Me | 139–141 |
| 4-04 | 4-F—Ph | S | $NMe_2$ | Me | Me | 172–174 |
| 4-05 | 4-F—Ph | S | $N^+Me_3(I^-)$ | Me | Me | 170–172 |
| 4-06 | 4-F—Ph | S | $NHCOCO_2Et$ | Me | Me | 152–154 |

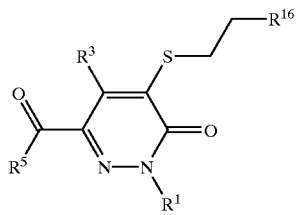

TABLE 5

| Compound No. | $R^1$ | X | $R^{16}$ | $R^3$ | $R^5$ | Melting point (° C.) |
|---|---|---|---|---|---|---|
| 5-01 | 4-F—Ph | S | $NHSO_2Me$ | Me | Me | paste |
| 5-02 | 4-F—Ph | S | $NHSO_2Ph$ | Me | Me | paste |
| 5-03 | 4-F—Ph | S | $OSO_2Me$ | Me | Me | 51–52 |
| 5-04 | 4-F—Ph | S | morpholino | Me | Me | 92–93 |
| 5-05 | 4-F—Ph | S | 2-piperidinoethyl | Me | Me | 56–57 |
| 5-06 | 4-F—Ph | S | $(CH_2)_2NHMe$ | Me | Me | 100–101 |
| 5-07 | 4-F—Ph | S | $(CH_2)_2NHOH$ | Me | Me | 103–105 |

NMR data of Compounds 5-01 and 5-02 are shown below.

| Compound No. | $^1$H-NMR (CDCl$_3$/TMS, δ value (ppm)) |
|---|---|
| 5-01 | 2.57 (3H, s), 2.69 (3H, s), 2.94 (3H, s), 3.28–3.45 (4H, m), 5.25 (1H, bs), 7.13–7.30 (2H, m), 7.54–7.65 (2H, m) |
| 5-02 | 2.56 (3H, s), 2.64 (3H, s), 3.15–3.30 (4h, m), 5.43 (1H, bs), 7.16–7.23 (2H, m), 7.41–7.90 (5H, m), 7.81–7.84 (2H, m) |

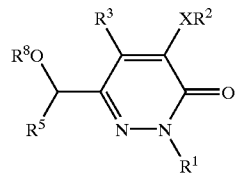

TABLE 6

| Compound No. | $R^1$ | X | $R^2$ | $R^3$ | $R^6$ | $R^8$ | Melting point (° C.) |
|---|---|---|---|---|---|---|---|
| 6-01 | 3-Cl-Ph | S | Ph | Me | Me | H | 180–182 |
| 6-02 | 4-F-Ph | S | 4-pyridyl | Me | Me | H | 194–196 |

Herein, in the symbols in Table, "Me", "Et", "iPr", "tBu", "Ac", "Ph" and "Bn" show a methyl group, an ethyl group, an isopropyl group, a tert-butyl group, an acetyl group, a phenyl group and a benzyl group, respectively.

Test Example (Test of Neutrophil Adhesion Inhibitory Activity)

To a 96 hole culture plate coated with keyhole limpet hemocyanin were added Dulbecco modified Eagle's media (DMEM, 25 μl) containing various concentrations of the test substance. The neutrophils isolated from human peripheral blood were labeled with fluorescence by means of 5,6-carboxyfluorescein diacetate, suspended into DMEM in a concentration of $1 \times 10^6$ cells/ml, and inoculated to the above plate in an amount of 50 μl. Then, after the addition of 25 μl of formylmethionyl-leucyl-phenylalanine (hereinafter referred to as "fMLP") (final concentration of 50 nM), the cells were cultured at 37° C. for a certain period of time to induce the adhesion of the neutrophils to the plate. After culturing, the plate was washed with phosphate-buffered physiological saline to remove the neutrophils which were not adhered. The adhered neutrophils were dissolved and then the fluorescence intensity was measured. Using the data of a non-stimulated group where the stimulation with fMLP was not carried out and an fMLP-stimulated group where the stimulation was carried out, the adhesion inhibition rate at each concentration of the test substance was determined according to the following equation. From the concentration-inhibition curve, 50% inhibitory concentration (IC50) was calculated. Table 7 shows the results Adhesion inhibition rate $(\%)=(Fmax-Fx)/(Fmax-Fo)\times 100$ Fx: the fluorescence intensity of the group treated with a test substance Fmax: the fluorescence intensity of the fMLP-stimulated group Fo: the fluorescence intensity of the non-stimulated group

TABLE 7

Test of neutrophil adhesion inhibitory (50% inhibition concentration)

| Compound No. | IC50 ($\mu$M) | Compound No. | IC50 ($\mu$M) |
|---|---|---|---|
| 1-01 | 0.016 | 1-32 | 0.165 |
| 1-03 | 0.027 | 1-64 | 0.004 |
| 1-04 | 0.619 | 1-68 | 0.007 |
| 1-05 | 0.032 | 1-69 | 0.222 |
| 1-06 | 0.040 | 1-70 | 0.018 |
| 1-07 | 0.020 | 1-73 | 0.032 |
| 1-08 | 0.139 | 1-74 | 0.048 |
| 1-10 | 0.093 | 1-80 | 0.668 |
| 1-11 | 0.079 | 1-83 | 0.012 |
| 1-12 | 0.007 | 1-84 | 0.010 |
| 1-15 | 0.058 | 1-97 | 0.011 |
| 1-16 | 0.017 | 1-98 | 0.656 |
| 1-17 | 0.019 | 1-100 | 0.410 |
| 1-20 | 0.005 | 1-102 | 0.310 |
| 1-21 | 0.196 | 1-113 | 0.358 |
| 1-22 | 0.009 | 1-115 | 0.044 |
| 1-23 | 0.006 | 1-130 | 0.138 |
| 1-24 | 0.014 | 1-134 | 0.463 |
| 1-25 | 0.010 | 1-151 | 0.975 |
| 1-26 | 0.139 | 6-01 | 0.009 |
| 1-31 | 0.055 | 6-02 | 0.306 |

Industrial Applicability

The present invention provides a pyridazinone derivative having a strong cell adhesion inhibiting activity and possessing an antiinflammatory activity, an antiasthmatic activity, an antirheumatic activity, an antiarteriosclerotic activity, an antiallergic activity, a suppressive activity of cancer metastasis, a suppressive activity of inflammatory disorder accompanying operation or treatment, a suppressive activity of ischemic reperfusion injury, a suppressive activity of rejection at organ transplantation, an antipsoriatic activity, a suppressive activity of acute pulmonary injury, a therapeutic activity of inflammatory intestinal disease, a therapeutic activity of burn and the like.

What is claimed is:
1. A pyridazinone derivative represented by formula (I):

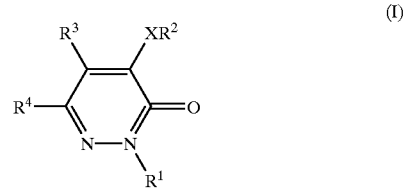

{wherein
R$^1$ represents a phenyl group, a substituted phenyl group having 1 to 5 substituents, which substitute the hydrogen atom(s) on the ring and are the same or different, selected from a (C$_1$–C$_8$)alkyl group, a halo (C$_1$–C$_8$) alkyl group, a (C$_1$–C$_8$)alkoxy group, a halo (C$_1$–C$_8$) alkoxy group, a (C$_1$–C$_8$)alkylthio group, a (C$_1$–C$_8$) alkoxycarbonyl group, a carbamoyl group, a cyano group, a nitro group, a halogen atom, a carboxyl group, a hydroxyl group, an amino group, an amino group substituted with one or two (C$_1$–C$_8$)alkyl groups which are the same or different, a 4- to 10-membered cyclic amino group which contains a nitrogen atom, an oxygen atom or a sulfur atom selected from a pyrrolidino group, a piperidino group, a piperazino group, an N-methylpiperazino group, an N-phenylpiperazino group, a morpholino group, a thiomorpholino group, a hexamethyleneimino group, or a 3,3,5-trimethylhexahydroazepino group, an aminocarbonyl group substituted with one or two (C$_1$–C$_8$)alkyl groups which are the same or different, a 4- to 10-membered cyclic aminocarbonyl group, a (C$_1$–C$_8$) alkylcarbonylamino group, a (C$_1$–C$_8$) alkoxycarbonylamino group, a hydroxyamino group, an N-acetylhydroxyamino group, an acetoxyamino group, a methylenedioxy group, an ethylenedioxy group, a (C$_1$–C$_8$)alkylsulfonylamino group, a phenylcarbonylamino group, a phenylcarbonylamino group having 1 to 5 substituents, which are the same or different, selected from a (C$_1$–C$_8$)alkyl group, a (C$_1$–C$_8$)alkoxy group, a cyano group, a nitro group or a halogen atom on the ring, an aromatic heterocyclic-carbonylamino group, an aromatic heterocyclic-carbonylamino group having 1 to 5 substituents, which are the same or different, selected from a (C$_1$–C$_8$)alkyl group, a (C$_1$–C$_8$)alkoxy group, a cyano group, a nitro group or a halogen atom on the ring, a phenylsulfonylamino group, a phenylsulfonylamino group having 1 to 5 substituents, which are the same or different, selected from a (C$_1$–C$_8$)alkyl group, a (C$_1$–C$_8$)alkoxy group, a cyano group, a nitro group or a halogen atom on the ring, an aromatic heterocyclic-sulfonylamino group, an aromatic heterocyclic-sulfonylamino group having 1 to 5 substituents which are the same or different, selected from a (C$_1$–C$_8$)alkyl group, a (C$_1$–C$_8$)alkoxy group, cyano group, nitro group or a halogen atom on the ring, an aromatic heterocyclic group or a substituted aromatic heterocyclic group having 1 to 5 substituents, which are the same or different, selected from a (C$_1$–C$_8$)alkyl group, a (C$_1$–C$_8$)alkoxy group, a (C$_1$–C$_8$)alkylthio group, a (C$_1$–C$_8$)alkoxycarbonyl group, a carboxyl group, a carbamoyl group, a cyano group, a nitro group or a halogen atom;
R$^2$ represents a (C$_1$–C$_8$)alkyl group, a substituted (C$_1$–C$_8$) alkyl group having one or more substituents, which are the same or different, selected from a halogen atom, a hydroxyl group, a $(C_1-C_8)$alkoxy group, a $(C_1-C_8)$ alkylthio group, a $(C_1-C_8)$alkoxycarbonyl group, a carboxyl group, a cyano group, a nitro group, an amino-group, a hydroxyamino group, an amino group substituted with one or two $(C_1-C_8)$alkyl groups which are the same or different, a 4- to 10-membered cyclic amino group having the same meaning as described above, a $(C_1-C_8)$alkylcarbonylamino group, a carbamoyl group, an aminocarbonyl group substituted with one or two $(C_1-C_8)$alkyl groups which are the same or different, a 4- to 10-membered cyclic aminocarbonyl group, a $(C_1-C_8)$alkylsulfonylamino group, a phenylcarbonylamino group, a phenylcarbonylamino having 1 to 5 substituents, which are the same or different, selected from a $(C_1-C_8)$alkyl group, a $(C_1-C_8)$alkoxy group, a $(C_1-C_8)$alkoxycarbonyl group, a cyano group, a nitro group or a halogen atom on the ring, an aromatic heterocyclic-carbonylamino group, an aromatic heterocyclic-carbonylamino group having 1 to 5 substituents, which are the same or different, selected from a $(C_1-C_8)$alkyl group, a $(C_1-C_8)$alkoxy group, a $(C_1-C_8)$alkoxycarbonyl group, a cyano group, a nitro group or a halogen atom on the ring, a phenylsulfonylamino group, a phenylsulfonylamino group having 1 to 5 substituents, which are the same or different, selected from a $(C_1-C_8)$alkyl group, a $(C_1-C_8)$alkoxy group, a $(C_1-C_8)$alkoxycarbonyl group, a cyano group, a nitro group or a halogen atom on the ring, an aromatic heterocyclic-sulfonylamino group, an aromatic heterocyclic-sulfonylamino group having 1 to 5 substituents, which are the same or different, selected from a $(C_1-C_8)$alkyl group, a $(C_1-C_8)$alkoxy group, a $(C_1-C_8)$alkoxycarbonyl group, a cyano group, a nitro group or a halogen atom on the ring, a phenyl group, a substituted phenyl group having the same meaning as described above, an aralkyl group, a substituted aralkyl group having an aryl ring or aromatic heterocycle substituted with 1 to 5 substituents, which are the same or different, selected from a $(C_1-C_8)$alkyl group, a $(C_1-C_8)$alkoxy group, a $(C_1-C_8)$alkoxycarbonyl group, a carboxyl group, a cyano group, a nitro group or a halogen atom, an aromatic heterocyclic group, a substituted aromatic heterocyclic group having the same meaning as described above, an amino group, an amino group substituted with one or two $(C_1-C_8)$alkyl groups which are the same or different, a 4- to 10-membered cyclic amino group having the same meaning as described above, a cyano group, a carboxyl group, a $(C_1-C_8)$alkoxycarbonyl group, a carbamoyl group, a thiocarbamoyl group, an aminocarbonyl group, an aminocarbonyl group substituted with one or two $(C_1-C_8)$ alkyl groups or substituted $(C_1-C_8)$alkyl groups which are the same or different, a 4- to 10-membered cyclic aminocarbonyl group, a phenylaminocarbonyl group, a substituted phenylaminocarbonyl group wherein the aminocarbonyl group is substituted with a phenyl group having the same meaning as the above-described substituted phenyl group, an aromatic heterocyle-aminocarbonyl group or a substituted aromatic heterocyle-aminocarbonyl group wherein the aminocarbonyl group is substituted with an aromatic heterocyclic group having 1 to 5 substituents, which are the same or different, selected from a $(C_1-C_8)$alkyl group, a $(C_1-C_8)$alkoxy group, a $(C_1-C_8)$alkylthio group, a $(C_1-C_8)$alkoxycarbonyl group, a carboxyl group, a carbamoyl group, a cyano group, a nitro group or a halogen atom;

$R^3$ represents a hydrogen atom, a $(C_1-C_8)$alkyl group, a substituted $(C_1-C_8)$alkyl group having the same meaning as described above, a phenyl group, a substituted phenyl group having the same meaning as described above, an aromatic heterocyclic group or a substituted aromatic heterocyclic group having the same meaning as described above;

$R^4$ represents a cyano group,

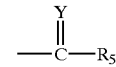

(wherein $R^5$ represents a hydrogen atom, a $(C_1-C_8)$alkyl group, a substituted $(C_1-C_8)$alkyl group having the same meaning as described above, a $(C_1-C_8)$alkoxy group, a hydroxyl group, amino group, an amino group substituted with one or two $(C_1-C_8)$alkyl groups which are the same or different, a 4- to 10-membered cyclic amino group having the same meaning as described above, phenyl group, a substituted phenyl group having the same meaning as described above, an aromatic heterocyclic group or a substituted aromatic heterocyclic group having the same meaning as described above, or $R^5$ may form $(CR^7{}_2)_m$ (wherein $R^7$ are the same or different and represents hydrogen atom, a $(C_1-C_8)$alkyl group, a substituted $(C_1-C_8)$alkyl group having the same meaning as described above, a phenyl group, a substituted phenyl group having the same meaning as described above, an aromatic heterocyclic group or a substituted aromatic heterocyclic group having the same meaning as described above, and m represents an integer of 2 to 7) together with $R^3$ to form a ring; and Y represents NH, O or S)

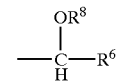

(wherein $R^6$ represents a hydrogen atom, a $(C_1-C_8)$alkyl group, a substituted $(C_1-C_8)$alkyl group having the same meaning as described above, a phenyl group, a substituted phenyl group having the same meaning as described above, an aromatic heterocyclic group or a substituted aromatic heterocyclic group having the same meaning as described above, or $R^6$ may form $(CR^7{}_2)_m$ (wherein $R^7$ and m have the same meanings as described above) together with $R^3$ to form a ring; and $R^8$ represents a hydrogen atom or a $(C_1-C_8)$ alkylcarbonyl group), or

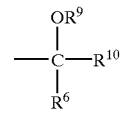

(wherein $R^6$ has the same meaning as described above; and $R^9$ and $R^{10}$ are the same or different and represent a $(C_1-C_8)$alkyl group or a substituted $(C_1-C_8)$ alkyl group having the same meaning as described above, or $R^9$ and $R^{10}$ together form a ($C_2$–$C_4$)alkylene chain and may form a ring together with the atoms attached thereto); and X represents a single bond, O or $S(O)_n$ (wherein n represents an integer of 0, 1 or 2)}, or a pharmaceutically acceptable salt thereof.

2. A pharmaceutical composition comprising as an active ingredient the derivative according to claim 1 or a pharmaceutically acceptable salt thereof, and a pharmaceutically acceptable carrier or diluent.

3. A method for inhibiting cell adhesion by administering an effective amount of the derivative according to claim 1 or a pharmaceutically acceptable salt thereof.

4. A method for treating or preventing a disease relating to cell adhesion by administering an effective amount of the derivative according to claim 1 or a pharmaceutically acceptable salt thereof, wherein the disease relating to cell adhesion is selected from the group consisting of inflammation, asthma, chronic articular rheumatism, arteriosclerosis, allergy, cancer metastasis, inflammatory disorder accompanying operation or treatment, ischemic reperfusion injury, rejection at organ transplantation, psoriasis, acute pulmonary injury, inflammatory intestinal disease, and burn.

5. The method according to claim 4, wherein the disease is inflammation, asthma, chronic articular rheumatism, arteriosclerosis, allergy, cancer metastasis, inflammatory disorder accompanying operation or treatment, ischemic reperfusion injury, rejection at organ transplantation, psoriasis, acute pulmonary injury, inflammatory intestinal disease, or burn.

* * * * *